(12) United States Patent
Fujimoto et al.

(10) Patent No.: US 8,128,889 B2
(45) Date of Patent: Mar. 6, 2012

(54) ANALYZING ARTICLE, ANALYZER AND METHOD OF ANALYZING A SAMPLE USING THE ANALYZING ARTICLE, AND A METHOD OF FORMING AN OPENING IN THE ANALYZING ARTICLE

(75) Inventors: Koji Fujimoto, Kyoto (JP); Shigeru Kitamura, Kyoto (JP); Masaki Hori, Kyoto (JP)

(73) Assignee: Arkray, Inc., Kyoto-shi (JP)

( * ) Notice: Subject to any disclaimer, the term of this patent is extended or adjusted under 35 U.S.C. 154(b) by 1196 days.

(21) Appl. No.: 10/514,010

(22) PCT Filed: Apr. 28, 2003

(86) PCT No.: PCT/JP03/05481
§ 371 (c)(1),
(2), (4) Date: Oct. 27, 2004

(87) PCT Pub. No.: WO03/093836
PCT Pub. Date: Nov. 13, 2003

(65) Prior Publication Data
US 2005/0282290 A1 Dec. 22, 2005

(30) Foreign Application Priority Data

Apr. 30, 2002 (JP) ................................ 2002-128952
Oct. 28, 2002 (JP) ................................ 2002-312962
Dec. 20, 2002 (JP) ................................ 2002-370927

(51) Int. Cl.
*B01L 3/00* (2006.01)
*G01N 35/00* (2006.01)

(52) U.S. Cl. ........ 422/417; 422/408; 422/413; 422/502; 436/165; 435/287.6; 435/288.5

(58) Field of Classification Search .................. None
See application file for complete search history.

(56) References Cited

U.S. PATENT DOCUMENTS 4,676,274 A    6/1987    Brown
(Continued)

FOREIGN PATENT DOCUMENTS
EP    0 977 032    2/2000
(Continued)

OTHER PUBLICATIONS

Shoji. *BME*, vol. 15, No. 10, pp. 51-56 (2001).
(Continued)

*Primary Examiner* — P. Kathryn Wright
(74) *Attorney, Agent, or Firm* — Day Pitney LLP

(57) ABSTRACT

The present invention relates to a technique for moving a mobile component such as a sample and a reagent, in an analyzing article. A method of analyzing a sample according to the present invention includes a first movement step of moving a mobile component from a fluid entrance port (61) to a first goal (511) in a passage (51), and a second movement step of moving the mobile component from the first goal (511) to a second goal (512) in the passage (51), in an analyzing article (Y1). The analyzing article (Y1) further includes a branch passage which branches from the first goal (511), and a first opening for releasing gas from within the branch passage. The first movement step is carried out by establishing communication between inside and outside of the branch passage via the first opening. The second movement step is carried out by providing a second opening downstream from the second goal (512) with respect to a flow direction of the mobile component, thereby establishing communication between inside and outside of the passage.

7 Claims, 39 Drawing Sheets
(4 of 39 Drawing Sheet(s) Filed in Color)

U.S. PATENT DOCUMENTS

| | | | |
|---|---|---|---|
| 4,849,340 A * | 7/1989 | Oberhardt | 435/13 |
| 5,230,866 A | 7/1993 | Shartle et al. | |
| 5,587,128 A | 12/1996 | Wilding et al. | |
| 5,681,529 A | 10/1997 | Taguchi et al. | |
| 5,759,866 A | 6/1998 | Machida et al. | |
| 6,001,307 A | 12/1999 | Naka et al. | |
| 6,197,494 B1 | 3/2001 | Oberhardt | |
| 6,716,002 B2 | 4/2004 | Higashino | |
| 7,560,073 B1 * | 7/2009 | Peters et al. | 422/99 |
| 2001/0001060 A1 * | 5/2001 | Kellogg et al. | 435/7.1 |
| 2002/0047003 A1 * | 4/2002 | Bedingham et al. | 219/388 |
| 2002/0106786 A1 * | 8/2002 | Carvalho et al. | 435/287.3 |
| 2003/0190265 A1 | 10/2003 | Anazawa et al. | |
| 2004/0096358 A1 * | 5/2004 | Blankenstein et al. | 422/58 |
| 2004/0265180 A1 * | 12/2004 | Cox et al. | 422/99 |

FOREIGN PATENT DOCUMENTS

| | | |
|---|---|---|
| JP | 4-188065 | 7/1992 |
| JP | 8-114539 | 5/1996 |
| JP | 9-196920 | 7/1997 |
| JP | 10-2875 | 1/1998 |
| JP | 10-132712 | 5/1998 |
| JP | 2001-322099 | 11/2001 |
| JP | 2002-219697 | 8/2002 |
| WO | WO99/46045 * | 9/1999 |
| WO | WO 00/22436 | 4/2000 |
| WO | WO 01/87487 | 11/2001 |
| WO | WO 02/11887 | 2/2002 |

OTHER PUBLICATIONS

Micro-Miniaturized Total Analysis System (μTAS), Research Ad Hoc Committee, Ed. "Technological Trend in Micro-Miniaturized Total Analysis System (μTAS)". *Technical Report of the Journal of the Institute of Electrical Engineers of Japan*, Issue 812, pp. 64-98 (Dec. 15, 2000).

* cited by examiner

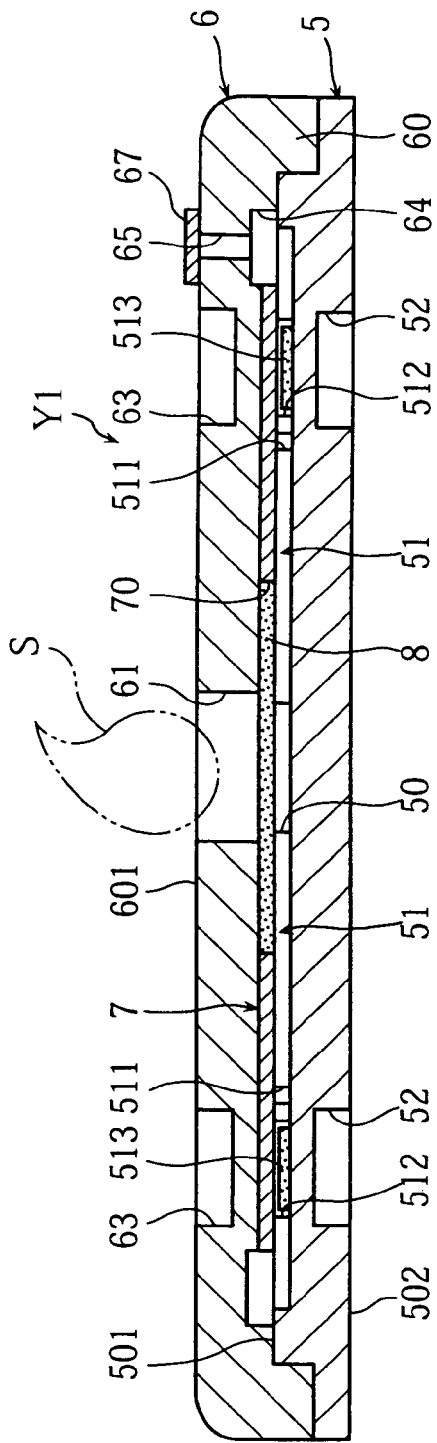
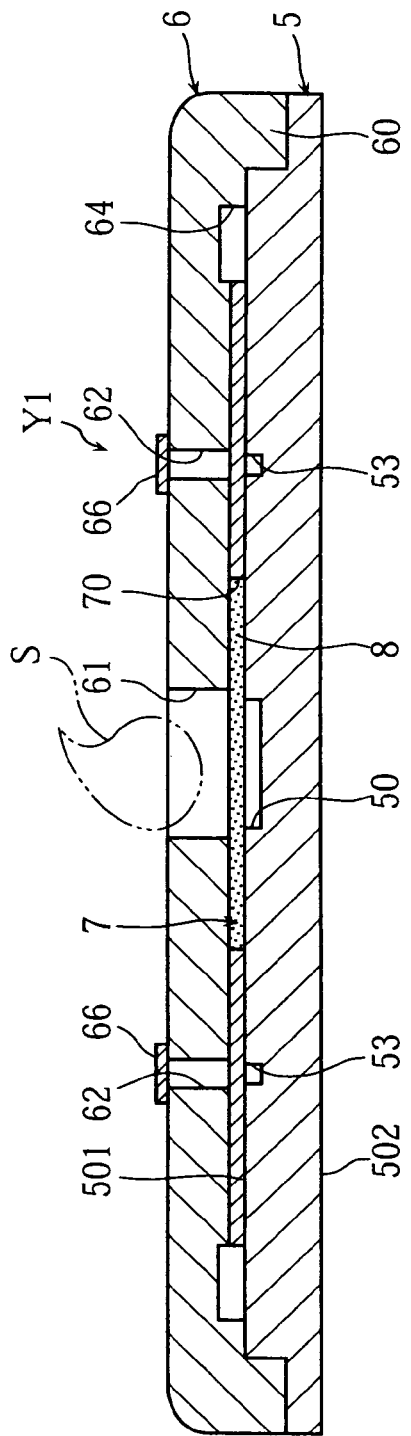

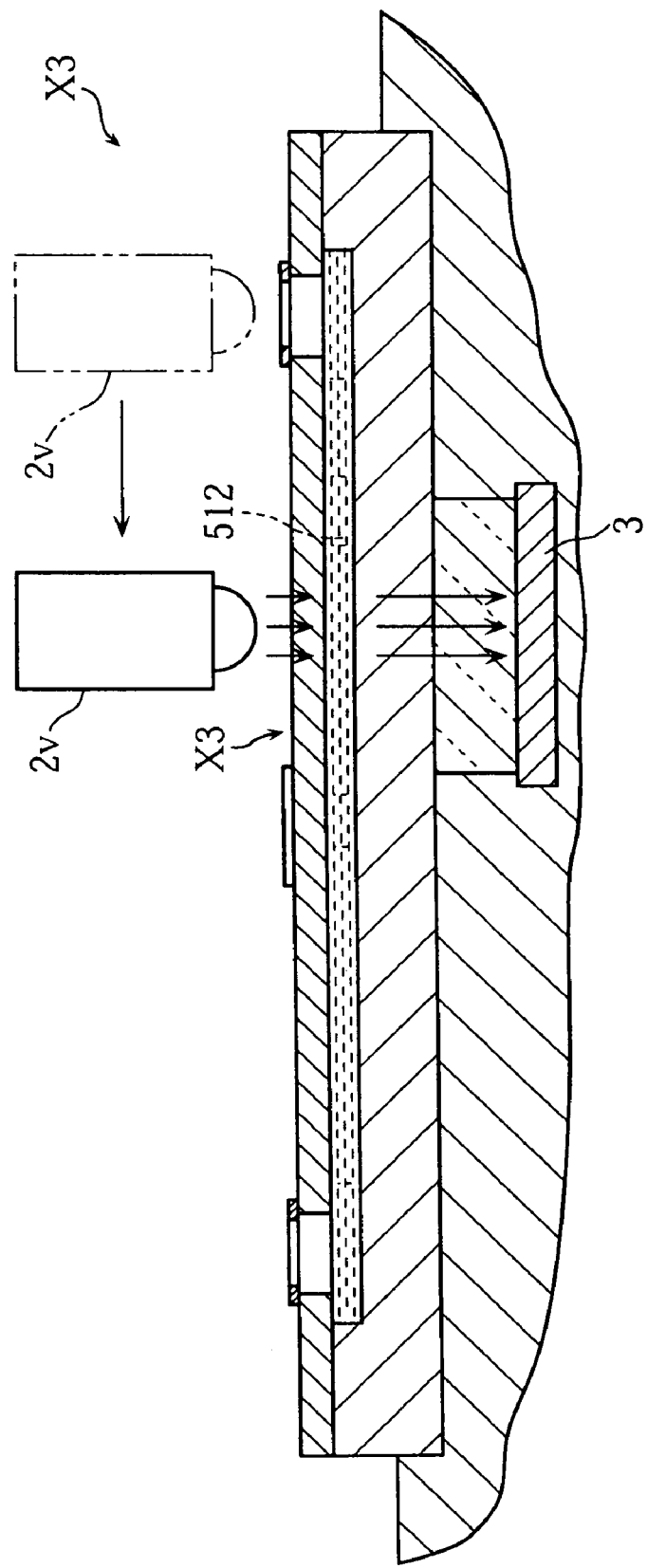

ANALYZING ARTICLE, ANALYZER AND METHOD OF ANALYZING A SAMPLE USING THE ANALYZING ARTICLE, AND A METHOD OF FORMING AN OPENING IN THE ANALYZING ARTICLE

The patent or application file contains at least one drawing executed in color. Copies of this patent or patent application publication with color drawing(s) will be provided by the Office upon request and payment of the necessary fee.

TECHNICAL FIELD

The present invention relates to a technique for moving a mobile component such as a sample and a reagent, in an analyzing article.

BACKGROUND ART

In a common method of analyzing a sample, the sample is allowed to react with a reagent, and a resulting reaction liquid is optically analyzed. In such a method, an analyzing article which provides a reaction field is used. Further, when analyzing a small amount of reagent, a special analyzing article called micro device which is formed with very fine passages is utilized.

An example of the micro device is shown in FIG. 45. A micro device 9A shown in the figure includes a reactor 92A which is placed in a passage 90A and includes a region holding a reagent 91A. A sample introduced from a sample entrance 93A is moved and supplied to the reactor 92A. The passage 90A has a rectangular cross section having a width ranging from 10-500 μm and a depth ranging from 5-500 μm. In the reactor 92A, the supplied sample makes a reaction with the reagent 91A. The movement of the sample from the sample entrance 93A to the reactor 92A is dependent upon capillarity so an air releasing hole 94A is provided as shown in the illustration.

Alternatively, the movement of the sample from the sample entrance 93A to the reactor 92A may be achieved by incorporating a micro pump, a micro valve and so on in the micro device (See for example, JP-A 2002-219697 and JP-A 2001-322099, as well as "Technological Trend in Micro/Miniaturized Total Analysis System (μTAS)" edited by the Micro/Miniaturized Total Analysis System (μTAS) Research Ad Hoc Committee, pp. 64-68, Issue 812, Technical Report of the Journal of the Institute of Electrical Engineers of Japan, Dec. 15, 2000).

In the analysis system where a sample reacts with the reagent 91A and where the sample is moved to the reactor 92A, it is sometimes necessary to control the time from the introduction of the sample into the sample entrance 93A to the time when the sample arrives at the reactor 92A, i.e. a start timing of the reaction. For example, there is a case where the introduction of the sample into the sample entrance 93A is used as a reference time and analysis is performed using the reactor 92A in a predetermined time duration from the reference time. In such a case, it is necessary that every time the measurement is made, the transport time from the sample entrance 93A to the reactor 92A is identical.

On the other hand, FIG. 46 shows a micro device 9B which is formed with a plurality of reactors 92B for measurement of a plurality of target components. (See JP-A 10-2875). In the illustrated micro device 9B, the reactors 92B are connected with a single sample entrance 93B. Thus, in order for each of the reactors 92B to begin a reaction at an identical timing, control must be made so that each mobile component will move from the sample entrance 93B and arrive at each reactor 92B in the same time duration.

Such a control on the transport time (reaction start timing) from the sample entrance to the reactor is relatively easy in a micro device which incorporates a micro pump, a micro valve and so on. However, formation of the micro pump and the micro valve requires complex steps and is not advantageous in terms of manufacturing cost. If the micro device is a disposable type, the micro pump and the micro valve will push up the cost of micro device to an unpractical level. On the contrary, a micro device which uses capillarity is easy to manufacture and has cost advantage, yet it is difficult to control the above mentioned transport time. Specifically, dimensional inconsistency in the passage will directly result in inconsistency in transport time, and the inconsistency in the transportation time becomes conspicuous as the distance increases from the sample entrance to the reactors.

An example of the analyzing article is shown in FIG. 47 and FIG. 48 of the present application. (See JP-A 8-114539 for example.) An analyzing article 9C shown in these figures includes sample treatment chambers 95Ca, 95Cb, optical measurement chambers 92Ca, 92Cb, and a waste liquid reservoir 96C. All of these chambers are connected by passages 90Ca-90Cd. The sample treatment chambers 95Ca, 95Cb hold regents 91Ca, 91Cb respectively within themselves. The sample treatment chamber 95Ca is connected with a sample receiving port 97C. The waste liquid reservoir 96C is connected with a pump connecting port 98C. In this analyzing article 9C, a sample introduced from the sample receiving port 97C reacts with the reagent 91Ca in the sample treatment chamber 95Ca, and then sucked by a pump to the optical measurement chamber 92Ca and then to the sample treatment chamber 95Cb successively. Once the sample reaches the sample treatment chamber 95Cb, the sample reacts with a reagent 91Cb in the sample treatment chamber 95Cb, and then transported to the optical measurement chamber 92Cb and to the waste liquid reservoir 96C successively.

A technique of using pump suction for transporting the sample is disclosed in JP-A 09-196920 for example.

In sample transportation by connecting a pump, it is not always easy to control the transport time (reaction start timing) due to pump pulsation and other factors. Especially in the micro device in which passages have a very small cross section, there is an increased level of difficulty in the transport time control.

In the analyzing article 9C, the sample receiving port 97C and the pump connecting port 98C are open. This poses a potential problem that the reagents 91Ca, 91Cb can be affected by moisture for example, depending on the type of the reagents 91Ca, 91Cb. Such a problem can be eliminated by closing the sample receiving port 97C and the pump connecting port 98C, so that the sample receiving port 97C and the pump connecting port 98C should only be opened upon analysis. However, there is no readily available technique of opening the sample receiving port 97C and the pump connecting port 98C with a simple structure and at a low cost. In fact, the sample receiving port 97C and the pump connecting port 98C may not be the only portions to be opened, and there can be a requirement that other regions must also be opened from a closed status, at the time of analysis.

DISCLOSURE OF THE INVENTION

The present invention aims at supplying a mobile component to a target region at a desired timing, by a simple construction manufacturable at an advantageous cost, in an analyzing article designed to move mobile components such as a sample and a reagent.

The present invention also aims at forming an opening cheaply and easily.

A first aspect of the present invention provides a method of analyzing a sample using an analyzing article. The analyzing article includes at least one passage for moving a mobile component introduced from a fluid entrance port. The method includes a first movement step of moving the mobile component from the fluid entrance port to a first goal in the passage, and a second movement step of moving the mobile component from the first goal to a second goal in the passage. The analyzing article further includes a branch passage which branches from the first goal, and a first opening for releasing gas from within the branch passage. The first movement step is carried out by establishing communication between inside and outside of the branch passage via the first opening. The second movement step is carried out by providing a second opening downstream from the second goal with respect to a flow direction of the mobile component thereby establishing communication between inside and outside of the passage.

The term "mobile component" used in the present invention includes components movable in the passage under capillarity, and may vary depending on the structure of the analyzing article. Examples are samples, reagents and carrier fluids for moving these.

If the analyzing article includes a plurality of passages, the second movement step is carried out simultaneously for these passages for example.

The analyzing article includes at least one gas releasing port which communicates with the passage and is closed by a closer before beginning of the second movement step. In this case, the second movement step is carried out, for example, by providing the second opening in the closer thereby opening the gas releasing port. Obviously, the analyzing article may not be formed with the gas releasing port in advance. In such a case, the passage and the outside may communicate with each other when the mobile component is moved beyond the second target in the second step, and the gas releasing port may be formed at the time of analysis.

When the analyzing article includes a plurality of passages, it is preferable that the second movement step is carried out simultaneously for the passages. Also, the first step may be performed simultaneously for the passages.

The present invention is suitable for cases in which analysis of a sample is made by using a micro device designed for analysis of a micro sample.

A second aspect of the present invention provides an analyzing article which includes a fluid entrance port, and at least one passage for moving a mobile component introduced from the fluid entrance port. The analyzing article further includes a branch passage branched from a branching region in the passage. The branch passage communicates with outside at a location other than the fluid entrance port, which prevents the mobile component from moving in the passage at the branching region. On the other hand, the passage communicates with outside at a location other than the fluid entrance port, which allows the mobile component to move in the passage beyond the branching region.

The passage communicates, for example, with a gas releasing port for releasing gas from within the passage. In this case, the gas releasing port is opened in order to allow the mobile component to move beyond the branching region.

The gas releasing port is closed by a closer for example. If the gas releasing port is formed in advance, the gas releasing port may be closed in advance by the closer, or the gas releasing port may be closed by the analyzer when the analyzing article is attached to the analyzer. The closing of the gas releasing port is carried out by placing a sheet member or a plug member for example. The opening operation of the gas releasing port is carried out by cutting or peeling the sheet member when the closer is provided by a sheet member, and by pulling off the plug when the closer is provided by a plug member. Alternatively, the plug member may be hollow and has a closed end, and the opening operation may be made by cutting the end of the plug member.

Obviously, the analyzing article may not be formed with the gas releasing port in advance. In such a case, the passage and the outside may communicate with each other when the mobile component is moved beyond the branching region, and the gas releasing port may be formed at the time of analysis.

The passage includes at least one reagent region containing a reagent for reaction with a sample.

The reagent region is located downstream from the branching region, for example, in the passage with respect to a flow direction of the mobile component. In this case, the distance between the reagent region and the branching region is smaller than that between the branching region and the fluid entrance port. More preferably, the branching region is in close proximity to the reagent region. According to this arrangement, it becomes possible to supply the mobile component from the branching region to the reagent region right away by simply opening the gas releasing port thereby letting the mobile component, which has been halted, move from the branching region in the passage. This arrangement enables to supply a mobile component (such as a sample) to a reaction zone at a desired timing, without relying upon a micro pump, a valve and so on which may otherwise have to be incorporated in the analyzing article.

If the analyzing article includes a plurality of passages, two or more of the passages, for example, each include a reagent region containing a reagent for reaction with a sample. In this case, preferably, the reagents contained in the reagent regions in the two or more passages are different from each other, so that the analyzing article allows measurements on a plurality of target components in a single sample.

A third aspect of the present invention provides an analyzing article which includes a fluid entrance port, and a plurality of passages for moving a mobile component introduced from the fluid entrance port. This analyzing article further includes a common passage which communicates with the passages, and at least one gas releasing port communicating with the common passage for releasing gas from within the passages via the common passage.

The fluid entrance port is provided at a center region for example. In this case, preferably, the passages allow the mobile component which has been introduced from the fluid entrance port to move from the center region toward a peripheral region. The passages run radially for example.

The analyzing article according to the present invention further includes a plurality of analysis regions for analysis of specific components in a sample fluid, and each passage includes at least one of the analysis regions. In this case, movement of the mobile component which has been introduced from the fluid entrance port is stopped upstream from the analysis region before being allowed into the analysis region.

The analyzing article according to the present invention preferably has the gas releasing port closed before the mobile component is introduced from the fluid entrance port. The gas releasing port is opened, whereby the mobile component is introduced into the analysis region.

The analyzing article according to the present invention has, for example, said at least one gas releasing port opened whereby the mobile component is prevented from entering the analysis regions.

The analyzing article according to the present invention may further include at least one additional gas releasing port and a plurality of branch passages. In this case, each of the branch passages communicates with said at least one additional gas releasing port and with a corresponding one of the passages before the analysis region. Said at least one additional gas releasing port is opened whereby the movement of mobile component is stopped before each of the analysis regions.

Two or more of the passages each include a reagent region which contains a reagent for reaction with a sample. The reagents contained in the reagent regions in the two or more passages are different from each other. In this case, the analyzing article allows measurements on a plurality of target components in a single sample.

A fourth aspect of the present invention provides an analyzing article which includes a fluid entrance port, a first common passage communicating with the fluid entrance port, a plurality of individual passages branched from the first common passage, a second common passage communicating with the individual passages, and a gas releasing port which communicates with the second common passage for releasing gas from within the individual passages via the second common passage. The gas releasing port is closed for allowing a mobile component into the first common passage, and then opened for supplying the individual passages with the mobile component simultaneously.

The analyzing article according to the second through the fourth aspects of the present invention is provided as a micro device for example. In this case, each passage includes a main cross section having a width of 10-500 μm and a depth of 5-500 μm. Further, the cross section is rectangular, and satisfies the inequality: depth/width$\geq$0.5. The term "main cross section" as used in the present invention is a vertical cross section perpendicular to the direction of flow of the sample fluid. If the cross section is not uniform, the term refers to a cross section of a part whose primary purpose is to let the mobile component pass.

A fifth aspect of the present invention provides an analyzer for analysis of a sample using an analyzing article which includes at least one passage for moving a mobile component introduced from a fluid entrance port. The analyzing article prevents the mobile component from moving beyond a first goal in the passage while allowing the mobile component to move beyond the first goal to a second goal in the passage by opening the passage at a location other than the fluid entrance port. The analyzer further includes an opener for opening the passage at a location other than the fluid entrance port.

The opener varies depending upon construction of a closer for example. For instance, if the analyzing article allows communication between inside and outside of the passage, and includes a gas releasing port closed by a closer, the opener is designed to open the gas releasing port by forming an opening in the closer. More specifically, if the closer is provided by a sheet member, the opener includes a needle, a blade or other forms of cutter for cutting the sheet member. If the closer is provided by a plug member inserted into the gas releasing port, then the opener includes a puller such as a clamp. Obviously, the opener may have other constructions. For instance, the opener may apply energy to the analyzing article without contacting the analyzing article thereby melting or deforming at least part of the analyzing article (causing shrinkage or warp for example). If the energy is applied in the form of light, the supply source of energy is preferably a laser. This enables energy application on a spot, making possible to make an opening selectively at a desired location.

A sixth aspect of the present invention provides an analyzer for analysis of a sample using an analyzing article which includes at least one passage for moving a mobile component introduced from a fluid entrance port. The analyzer includes a mount for attaching the analyzing article. The analyzing article further includes a branch passage branched from a branching region in the passage, and a gas releasing port for releasing gas from within the passage. The branch passage communicates with outside at a location other than the fluid entrance port whereby the mobile component is prevented from moving in the passage at the branching region. On the other hand, the passage communicates with outside at a location other than the fluid entrance port whereby the mobile component is allowed to move in the passage beyond the branching region. The analyzer further includes an opener and closer for selection of an open state and a closed state of the gas releasing port.

The opener and closer includes a movable closing element, for example. The selection of the open state and the closed state is made by moving the closing element.

A seventh aspect of the present invention provides a method of forming an opening in an analyzing article including a passage for moving a sample, for establishing communication between inside and outside of the passage. The method includes irradiating a target region in the analyzing article with light and allowing the target region to absorb optical energy.

The analyzing article to which the present invention is applied includes a communicating hole which communicates the inside of the passage with the outside, and a blocker which blocks the communicating hole and includes the target region.

The communicating hole serves, for example, as a gas releasing port for releasing gas from within the passage for moving the sample inside the passage, or the communicating hole serves as a fluid entrance port for introducing a sample or a regent into the passage.

The blocker is formed of a thermoplastic resin containing an additive for increased absorption of the light thrown to the blocker.

The thermoplastic resin preferably has a melting temperature not higher than 100° C. so that the amount of energy to be applied to the blocker may be small. More preferably, the thermoplastic resin has a melting temperature not higher than 85° C. From a practical point of view, the thermoplastic resin preferably has a melting temperature between 50° C.-85° C. If the melting temperature is excessively low, the blocker can soften or melt during storage. On the other hand, if the melting temperature is excessively high, a large amount of energy has to be applied as mentioned above, which leads to a disadvantage in terms of running cost.

The thermoplastic resin usable in the present invention is anything as long as the objective is fulfilled. Examples of the resin include homopolymers (straight polymers) or polymers of a single monomer, copolymers, and polymer alloys. By selecting a combination and a mixing ratio of copolymers or polymer alloys, it is possible to obtain a thermoplastic resin which has a desired melting temperature.

The homopolymer may be provided by low-melting-point (nylon) polyamide resins. The copolymer is preferably provided by one of ethylene resins such as ethylene-vinyl acetate copolymers and ethylene ionomers. In ethylene-vinyl acetate copolymers, the melting temperature can be lowered by increasing the amount of vinyl acetate content. For instance, a 6% content of vinyl acetate will give a melting temperature of about 100° C. whereas a 28% content of vinyl acetate will give a melting temperature of about 58° C. A ethylene-vinyl acetate copolymer used in this application typically has a 5-35% content of vinyl acetate. Ethylene ionomers are metallic salts of a copolymer between ethylene and unsaturated carboxylic acid. By selecting a kind of metallic salt and a monomer ratio, it is possible to obtain a thermoplastic resin which has a desired melting temperature between 80-100° C. Examples of the metal for the salt include Zn and Na.

The blocker which blocks an opening may be stretched thereby being in a tensioned state. With this arrangement, the tension in the material helps formation of the opening, making possible to form the opening with a smaller amount of optical energy. In this case, the thermoplastic resin is provided by an elastomer entirely, or by a plastomer which is given elasticity through alloying with an elastomer.

On the other hand, the additive is provided typically by a colorant. Although a variety of known coloring products can be used as the colorant, a selection is made on the basis of wavelength of the light to be applied to the blocker. Specifically, the selection should be made to achieve a near 100% light absorption at the blocker, and preferably the light absorption rate is not lower than 90%. For example, if the blocker receives a red light, then a green or black colorant is used. The green colorant can be provided typically by cobalt green ($CoO.Al_2O_3.Cr_2O_3$) and titanium-cobalt green ($TiO_2.CoO.NiOAnO$). Other options include copper phthalocyanine colors, perylene oil-soluble dyestuff. The black colorant can be provided typically by carbon black (C), copper-chromium black ($CuO.Cr_2O_3$), copper-iron black ($CuO.Fe_2O_3$) and iron black ($FeO_4$). Other options include anthraquinone organic pigments. The additive may be provided by still another, i.e. metal powder of copper and nickel typically. The amount of content of the additive is e.g. 1.0-3.0 weight parts to 100 weight parts of the thermoplastic resin.

The blocker preferably is formed as a sheet which has a thickness of 5-100 μm. If the thickness is excessively small, light cannot be absorbed sufficiently, whereas if the thickness is excessively large, thermal energy dissipates from the region hit by the light, making impossible to increase the temperature of the target region efficiently.

The blocker may include a heat storage filler in order to reduce dissipation of optical energy from the target region and to increase the temperature of the target region efficiently. Examples of the heat storage filler are metals such as gold, silver, copper, nickel and aluminum, as well as carbon black and glass. The heat storage filler preferably is granular or fibrous for example. Alternatively, the blocker may be provided by a mesh having a high heat storage capacity. The thermoplastic resin and the colorant are supported by the mesh. The mesh can be provided by a synthetic resin fiber, natural fiber or glass fiber. When using a heat storage filler and/or a mesh, these may be colored in the same color as the thermoplastic resin. Use of a filler and a mesh may also be made if the blocker is formed into a sheet, for improved ease of handling when the blocker is formed in the analyzing article.

The light irradiation to target regions such as the blocker is made by using a light source. The light source is preferably provided by a laser diode, which enables to make an opening with a small amount of electricity. Preferably, the laser diode is a single color light source capable of emitting a red, green, blue, infrared or ultraviolet ray, but laser diodes which emit combined light such as white light are also usable. The diameter of beam spot, output power and application time duration of the laser beam depend on the thickness, light absorption rate and so on of the blocker. Typically however, the laser beam is applied onto a diameter of 50-300 μm, at an output level of 15-50 mW for a time duration of 0.5-10 seconds. Alternatively to the laser diode, the light source may be provided by a light emitting diode, a halogen lamp, a xenon lamp, a tungsten lamp and so on.

If the analyzing article is designed for optical analysis of a sample, the light source of the light for the analysis may also be used as the light source of the light thrown to the target region.

BRIEF DESCRIPTION OF THE DRAWINGS

FIG. 5A is a sectional view taken in lines Z2-Z2 in FIG. 3. FIG. 5B is a sectional view taken in lines Z3-Z3 in FIG. 3.

FIG. 39 is a sectional view for describing a method of analyzing a sample.

FIG. 41A shows an opening formed by a 0.5 second application of a laser beam whereas FIG. 41B shows an opening formed by a 0.6 second application of the laser beam.

FIG. 42A shows an opening formed by a 0.5 second application of a laser beam whereas FIG. 42B shows an opening formed by a 0.8 second application of the laser beam.

FIG. 43A shows an opening formed by a 1.0 second application of a laser beam whereas FIG. 43B shows an opening formed by a 2.0 second application of the laser beam.

FIG. 44A shows an opening formed by a 1.0 second application of a laser beam whereas FIG. 44B shows an opening formed by a 3.0 second application of the laser beam.

BEST MODE FOR CARRYING OUT THE INVENTION

Hereinafter, best modes for carrying out the present invention will be described specifically, with reference to the drawings.

First, a first mode of embodiment of the present invention will be described.

Figure 1:
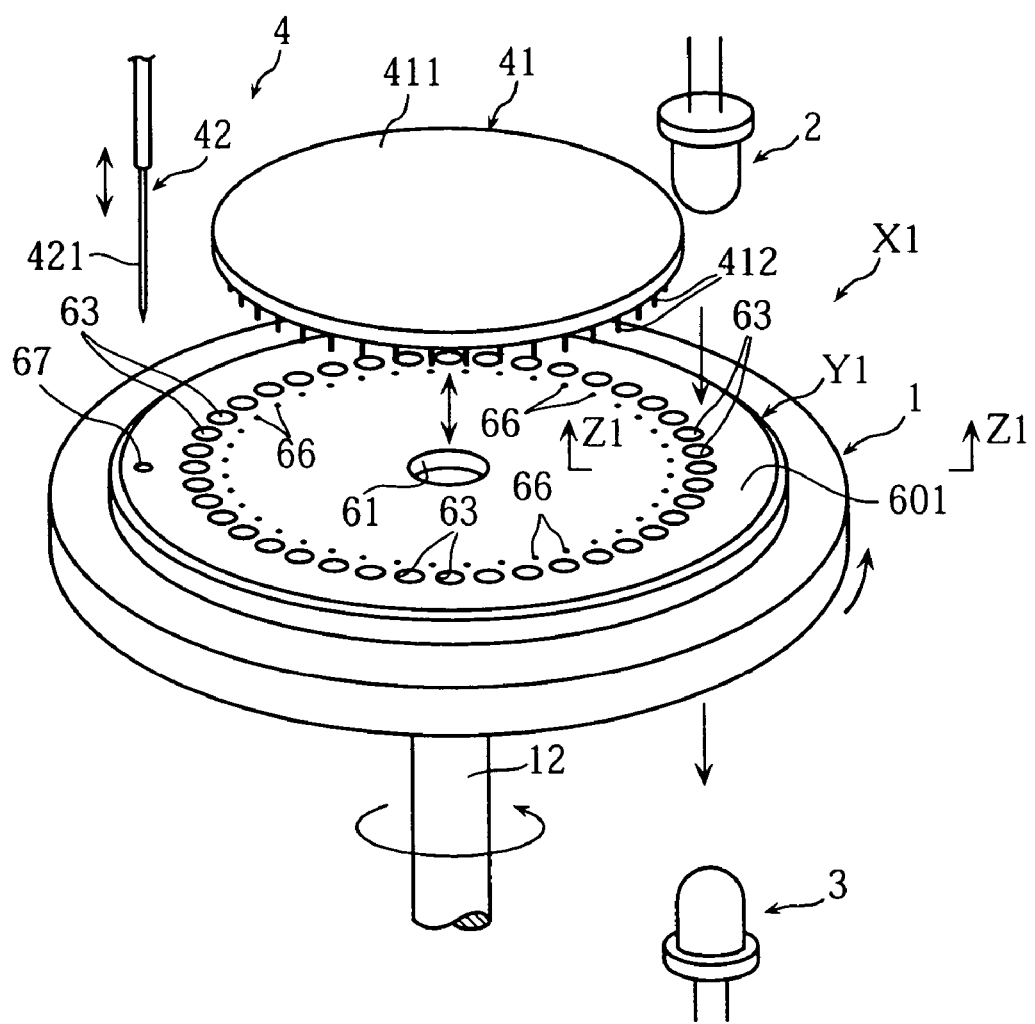
FIG. 1 illustrates a construction of an analyzer and an analyzing article according to a first embodiment of the present invention.
Figure 2:
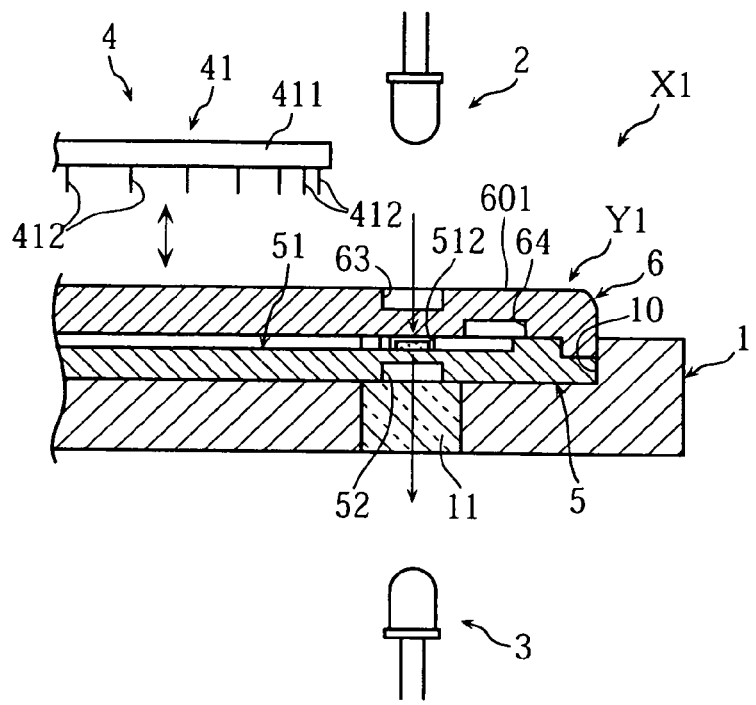
FIG. 2 is a sectional view taken in lines Z1-Z1 in FIG. 1.

FIG. 1 and FIG. 2 show an analyzer X1 which analyzes a sample fluid by using an analyzing article provided by a micro device Y1. The analyzer includes a mount 1 for attaching the micro device Y1, a light source 2, a light receiver 3 and an opening mechanism 4.

Figure 3:
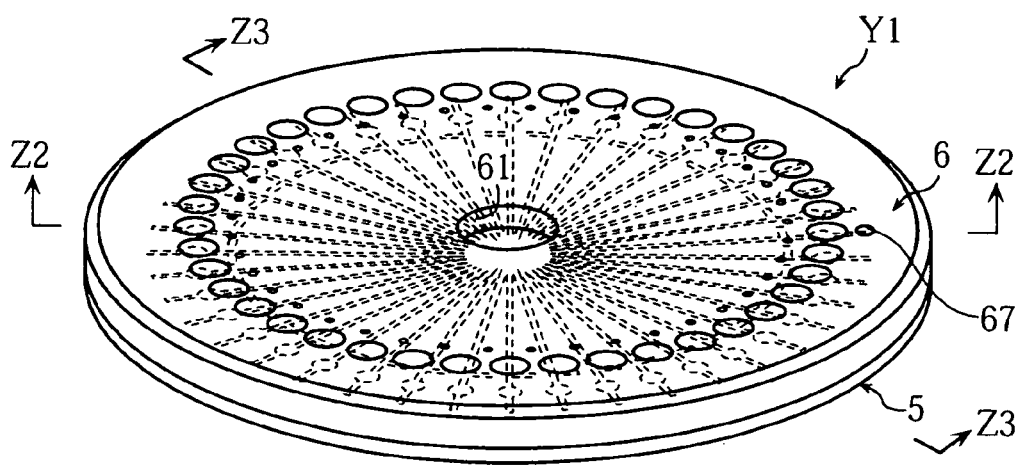
FIG. 3 is an overall perspective view of the micro device in FIG. 1.
Figure 4:
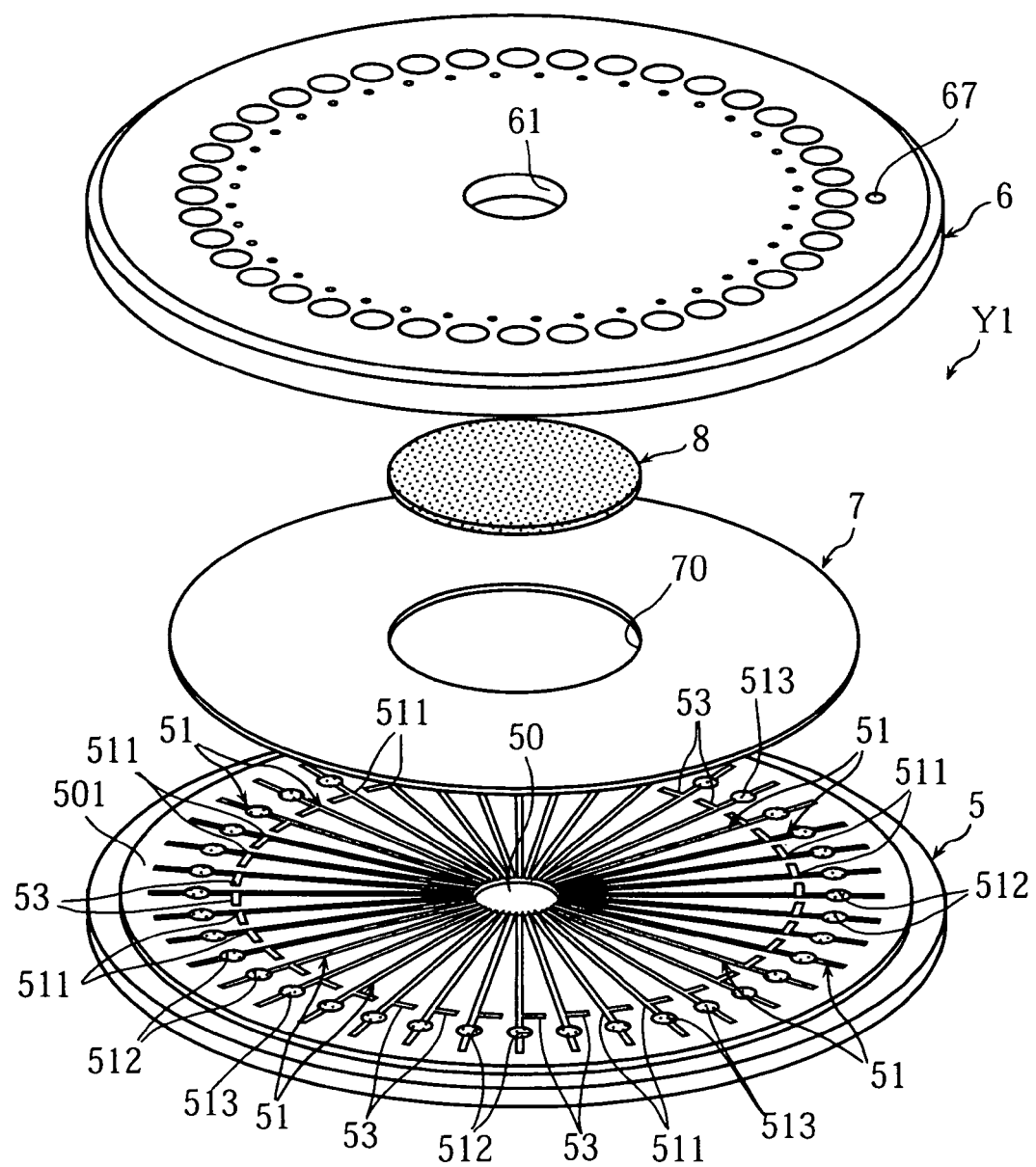
FIG. 4 is an exploded perspective view of the micro device in FIG. 3.

As shown in FIG. 3 through FIG. 5, the micro device Y1 provides a reaction field, and includes a substrate 5, a cover 6, an adhesion layer 7 and a separation sheet 8.

Figure 6:
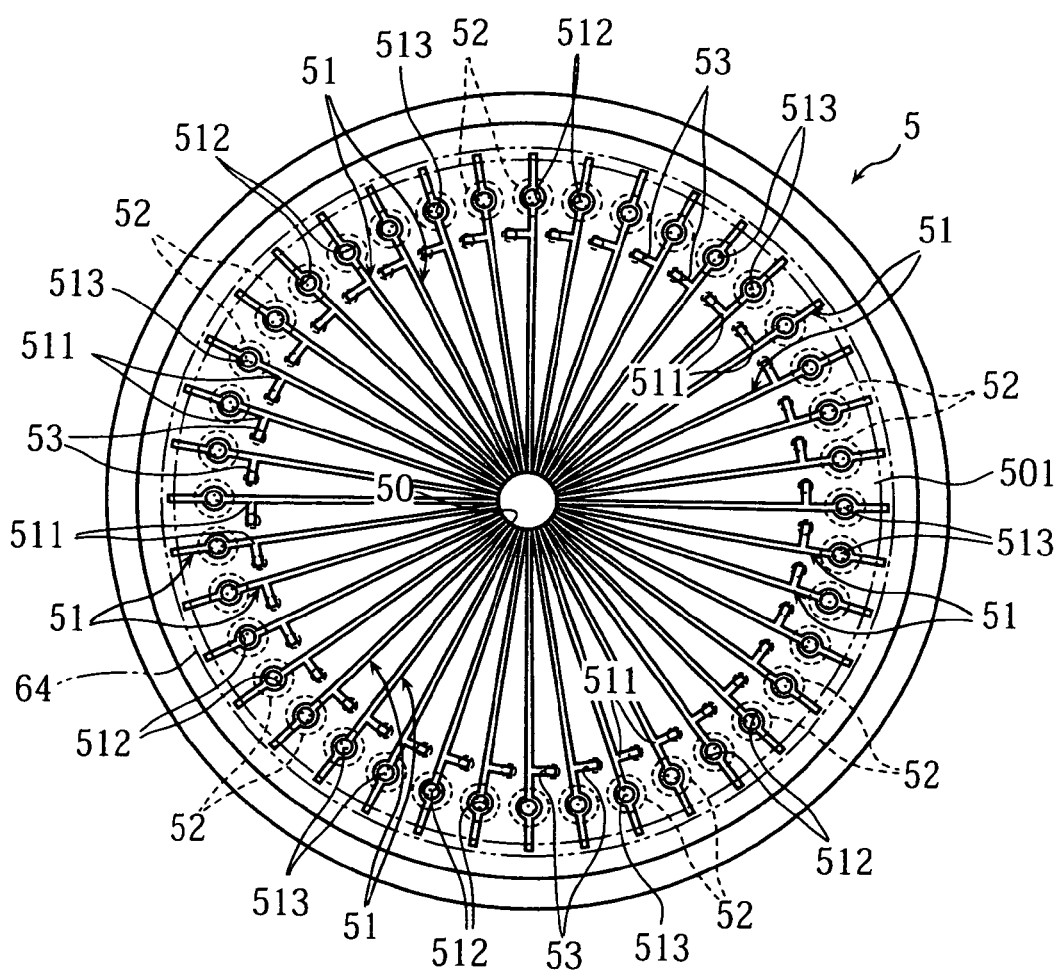
FIG. 6 is a plan view of a substrate of the micro device.

The substrate 5 is a transparent disc, having a down-stepped circumferential edge. As shown in FIG. 5 and FIG. 6, the substrate 5 has a fluid receiver 50 provided at a center region, a plurality of passages 51 communicating with the fluid reservoir 50 and extending radially from the fluid reservoir 50 toward the circumferential edge of the substrate 5, a plurality of recesses 52, and a plurality of branch passages 53.

The fluid reservoir 50 holds a sample fluid supplied to the micro device Y1, for introduction to each passage 51. The fluid reservoir 50 is a circular recess formed in an upper surface 501 of the substrate 5.

Each passage 51 is a transport channel for the sample fluid, communicates with the fluid reservoir 50, and is formed in the upper surface 501 of the substrate 5. As shown in FIG. 5A, each passage 51 has a branching region 511 and a reactor 512. Each passage 51 has a generally rectangular cross section except for the reactor 512. Each passage 51 is formed so that the rectangular section will have a width of e.g. 10-500 μm and a depth of e.g. 5-500 μm, and a width/height ratio not smaller than 0.5.

As shown in FIG. 4 and FIG. 6, the branch passage 53 extends from the branching region 511. The branching region 511 is formed as close as the reactor 512, so that the distance between the branching region 511 and the reactor 512 is as small as possible. The branch passage 53 has a generally uniform, rectangular cross section having similar dimensions to those of the passages.

The reactor 512 has a larger cross section than the passage 51. All of the reactors 512 are on the same circle. As shown in FIG. 5A, each reactor 512 is provided with a reagent region 513. However, the reagent region 513 may not necessarily be provided in all of the passages 51. For example, the reagent region is not provided in a passage which is used for correcting color influences from the sample fluid.

The reagent region 513 is solid, dissolved upon introduction of a sample fluid, and reacts with a specific component in the sample fluid for colorization. In the present mode of embodiment, a plurality of reagent regions 513 having different ingredients or compositions for example, are provided so that a plurality of target components can be measured.

The recesses 52 allow a light to pass through from the upper surface 501 through a lower surface 502 of the substrate 5 when the light is thrown on the reactor 512 as will be described later (See FIG. 1 and FIG. 2). Each recess 52 is formed in the lower surface 502 of the substrate 5, correspondingly to one of the reactors 512. As a result, as shown in FIG. 6, all of the recesses 52 are on the same circle along the circumferential edge of the substrate 5.

The substrate 5 is formed of a transparent resin such as an acrylic resin provided by e.g. polymethylmethacrylate (PMMA), and polydimethylsiloxane (PDMS). The liquid receiver 50, the passages 51, the recesses 52 and the branch passages 53 can be formed simultaneously at the time of molding the resin, by using a metal mold so designed.

The liquid receiver 50, the passages 51, and the branch passages 53 preferably have their inner surfaces treated for hydrophilicity. The hydrophilicity treatment may be performed using a variety of known methods. A preferred example, however, is first exposing the inner surfaces to a gas mixture including fluorine gas and oxygen gas, and then exposing the surfaces to water or water vapor. Since this method uses gas and water, a more reliable hydrophilicity treatment is possible to upright surfaces (side walls of the passages for example) than by ultra violet ray radiation which is also a known method for hydrophilicity treatment. The treatment is made so that each inner surface makes contact with pure water at an angle of 0-80 degrees.

The cover 6 is a disc which has a downwardly extending circumferential edge. The extended region 60 of the cover 6 makes contact with the down-stepped edge of the substrate 5. As shown in FIG. 5A and FIG. 5B as well as FIG. 7, the cover 6 has a sample fluid entrance port 61, a plurality of first gas releasing ports, a plurality of recesses 63, a common passage 64 and a second gas releasing port 65.

The fluid entrance port 61 is used for introducing a sample fluid, and is provided as a through hole. As shown clearly in FIG. 5, the fluid entrance port 61 is at a center region of the cover 6 and right above the fluid reservoir 50 in the substrate 5.

Figure 7:
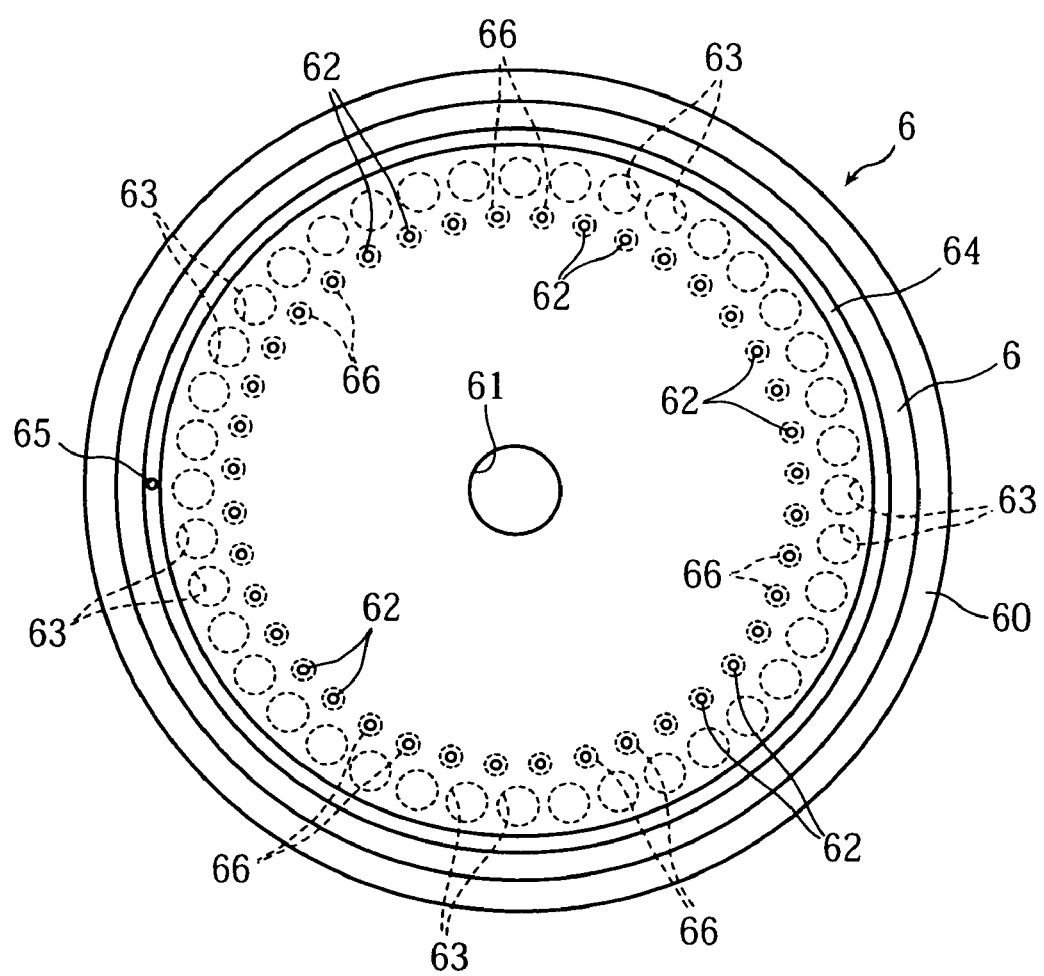
FIG. 7 is a bottom view of a cover of the micro device.

Each first gas releasing port 62 allows gas to escape from the passage 51, and is formed as a through hole. As shown clearly in FIG. 5B, each first gas releasing port 62 is right above one of the branch passages 53 in the substrate 5. As a result, all of the first gas releasing ports 62 are on the same circle as shown in FIG. 4 and FIG. 7. As shown clearly in FIG. 5B, each gas releasing port 62 has an upper opening closed by a sealing member 66. The sealing member 66 can be formed of a metal such as aluminum or a resin. The sealing member 66 is fixed onto the substrate 5 with an adhesive or by fusing for example.

The recesses 63 are regions through which a light is thrown to the reactors 512 from the side of an upper surface 601 of the cover 6, as will be described later (See FIG. 1 and FIG. 2). As shown in FIG. 5A, each recess 63 on the upper surface 601 of the cover 6 is right above one of the reactors 512. As a result, as shown in FIG. 4 and FIG. 7, the recesses 63 are on the same circle along the circumferential edge of the cover 6.

The common passage 64 serves as a passage for releasing gas from inside of the passages 51 to the outside, providing a channel for the gas to move to the second gas releasing port 65. As shown in FIG. 5 and FIG. 7, the common passage 64 is an annular recess along the circumferential edge of the cover 6. As shown in FIG. 5A and FIG. 6, the common passage 64 communicates with the passages 51 of the substrate 5.

In the micro device Y1, the common passage 64 is formed in the cover 6, and the passages 51 are formed in the substrate 5. This appropriately prevents the sample that has moved through the passage 51 from flowing into the common passage 64. As a result, it becomes possible to reduce a problematic case where the sample which has moved through a certain passage 51 flows back via the common passage 64 into another passage 51.

The common passage 64 may not be provided in the cover 6 but in the substrate 5. In this case however, it is preferable that the common passage and the passages have different depth from each other. This arrangement provides a step between the passages and the common passage, making possible to prevent the sample from flowing into the common passage.

The second gas releasing port 65 is, as shown in FIG. 5 and FIG. 7, a through hole which communicates with the common passage 64. The upper opening of the second gas releasing port 65 is closed by a sealing member 67. The sealing member 67 may be of the same material and make as is the sealing member 66 which closes the gas releasing port 62.

The cover 6 can be formed with a transparent resin material as is the substrate 5. The fluid entrance port 61, the first gas releasing ports, the recesses 63, the common passage 64 and the second gas releasing port 65 can be formed simultaneously at the time of molding the resin. At least regions of the cover 6 which are exposed to the passages 51 of the substrate 5 are preferably treated for hydrophilicity. The hydrophilicity treatment can be performed in the same way as for the substrate 5.

As clearly shown in FIG. 5 and FIG. 5B, the adhesion layer 7 provides adhesion between the cover 6 and the substrate 5. As shown in FIG. 4, FIG. 5A and FIG. 5B, the adhesion layer 7 is an adhesive sheet placed between the substrate 5 and the cover 6, and has a center region formed with a through hole 70. The through hole 70 of the adhesion layer 7 has a diameter greater than that of the fluid reservoir 50 in the substrate 5, and of the fluid entrance port 61 in the cover 6. The adhesive sheet can be a substrate having two surfaces each formed with an adhesive layer.

The separation sheet 8 separates solid components in the sample fluid (blood cell components in the blood for example). As shown in FIG. 5A and FIG. 5B, the separation sheet 8 has a diameter matched with the diameter of the through hole 70 of the adhesion layer 7, and is fitted into the through hole 70 of the adhesion layer 7 thereby placed between the fluid reservoir 50 of the substrate 5 and the fluid entrance port 61 of the cover 6. Since the fluid reservoir 50 is formed as a recess, the separation sheet 8 is spaced from the bottom of the fluid reservoir 50. Since the separation sheet 8 has a diameter matching the diameter of the through hole 70 which is greater than that of the fluid reservoir 50, the separation sheet 8 covers part of all passages 51 closest to the fluid reservoir 50. Because of such a layout of the separation sheet 8, the sample fluid coming from the fluid entrance port 61 first get filtration in the direction of thickness of the separation sheet 8 before reaching the fluid reservoir 50.

The separation sheet 8 can be provided by a porous material for example. The porous materials usable as the separation sheet 8 include, for example, paper, foam (foamed resin), woven materials, non-woven materials, knitted materials, membrane filter, glass filter, and gels. If the sample is supposed to be blood, and the separation sheet 8 is supposed to separate blood cell components, then the separation sheet 8 preferably has a hole size (pore size) ranging from 0.1-10 μm.

The mount 1 shown in FIG. 1 and FIG. 2 has a recess 10 for holding the micro device Y1. The mount 1 also has a light passing region 11. The light passing region 11 becomes inline with the reactor 512 when the micro device Y1 is attached to the recess 10. The light passing region 11 is provided by e.g. a transparent resin which is placed at an appropriate position in the mount 1. Obviously, the mount 1 may be made of a transparent material entirely. The mount 1 is supported by a rotating shaft 12, and by rotating the rotating shaft 12, the mount 1 is rotated. The rotating shaft 12 is connected with a drive mechanism which is placed out of the sight of the figure, and is driven to click by a rotating angle at which the reactors 512 are pitched on the micro device Y1.

The light source 2 throws light to the reactors 512 of the micro device Y1, and is fixed to face the recess 63 of the cover 6. The light source 2 is provided by a mercury lamp or a white-light LED for example. If these light sources are used, the light from the light source 2 is filtered by an unillustrated filter before being thrown to the reactor 512. The filter selects a range of predetermined wavelengths appropriate for light absorption characteristics of the analysis target in the reaction fluid.

The light receiver 3 receives the light which has passed the reactor 512, being fixed inline with the light source 2, to be able to face the recess 52 of the substrate 5. The amount of light received by the light receiver 3 provides a reference when making analysis (e.g. calculating the concentration) of the sample fluid. The light receiver 3 is provided by a photodiode for example.

The opening mechanism 4 has a first opener 41 for making an opening in the sealing member 66, and a second opener 42 for making an opening in the sealing member 67. These openers 41, 42 are reciprocable vertically by actuators which are placed out of the sight of the figures.

Figure 8:
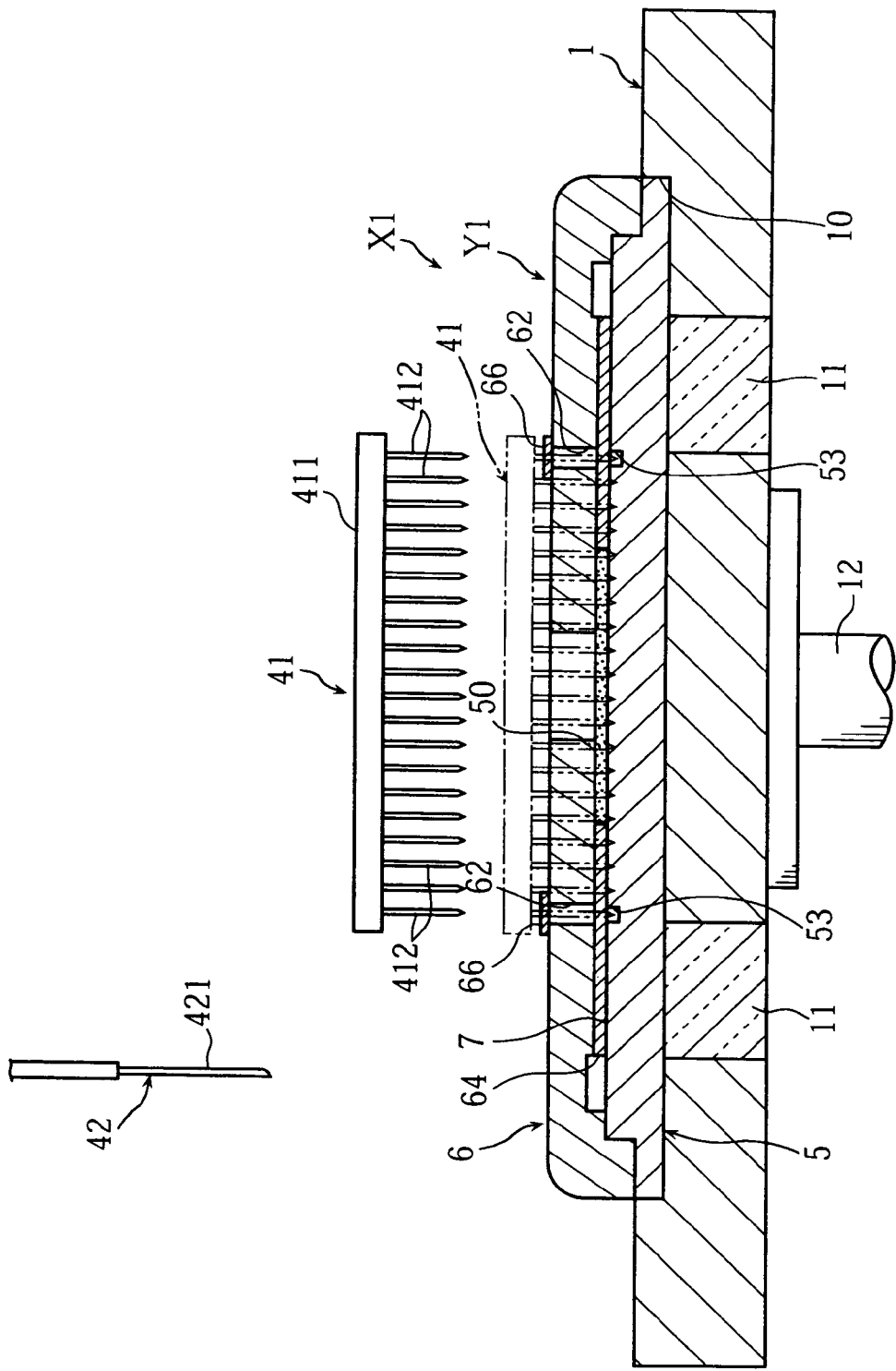
FIG. 8 is a sectional view for describing an operation of opening a first gas-releasing port.

The opening mechanism 41 includes a disc shaped substrate 411 which has a lower surface provided with a plurality of needles 412 protruding in a downward direction. As shown in FIG. 8, the needles 412 have a diameter which is smaller than that of the gas releasing port 62 in the cover 6. The needles 412 are placed on a circle so each faces one of the gas releasing ports 62. Thus, by aligning the needles 412 of the opening mechanism 41 with their corresponding gas releasing ports 62 of the cover 6 and then lowering the opening mechanism 41, it is possible to make an opening in all of the sealing members 66 simultaneously. This opens up the gas releasing ports 62, making each of the passages 51 communicating with outside via the branch passage 53 and the gas releasing port 62.

Figure 9:
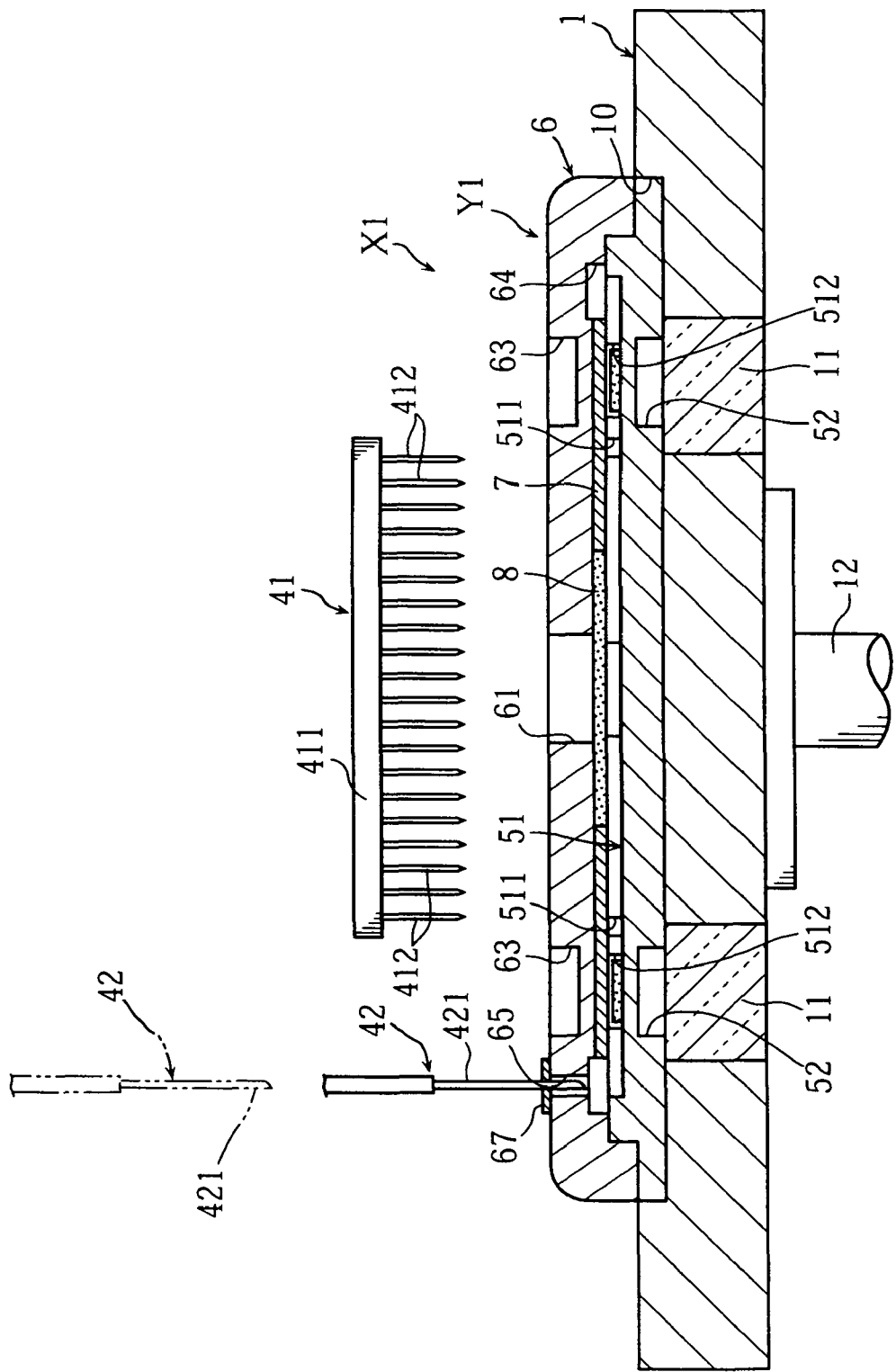
FIG. 9 is a sectional view for describing an operation of opening a second gas releasing port.

As shown in FIG. 1 and FIG. 9, the opening mechanism 42 has a needle 421. The needle 421 has a diameter which is smaller than that of the second gas releasing port 65 in the cover 6. Thus, by aligning the needle 421 of the opening mechanism 42 with the second gas releasing port 65 of the cover 6 and then lowering the opening mechanism 42, it is possible to make an opening in the sealing member 67. This opens up the second gas releasing port 65, making each of the passages 51 communicate with outside via the common passage 64 and the second gas releasing port 65.

Obviously, there is no limitation to the method of opening each of the first and the second gas releasing ports 62, 65. For example, the sealing members 66, 67 may be melted or deformed by energy, to open the first and the second gas releasing ports 62, 65. The application of the energy may be made by using e.g. light such as a laser, sound provided by an ultrasonic wave generator, and a heater. Peeling the sealing members 66, 67 of course is another method of opening the first and the second gas releasing ports 62, 65.

When analyzing, as shown in FIG. 5, it is necessary to supply the micro device Y1 with a sample fluid S via the fluid entrance port 61. Although the supply of the sample fluid S may be made after the micro device Y1 has been attached to the analyzer X1, preferably, the sample fluid S is supplied to the micro device Y1 in advance, and thereafter the micro device Y1 is attached to the analyzer X1.

Figure 10A:
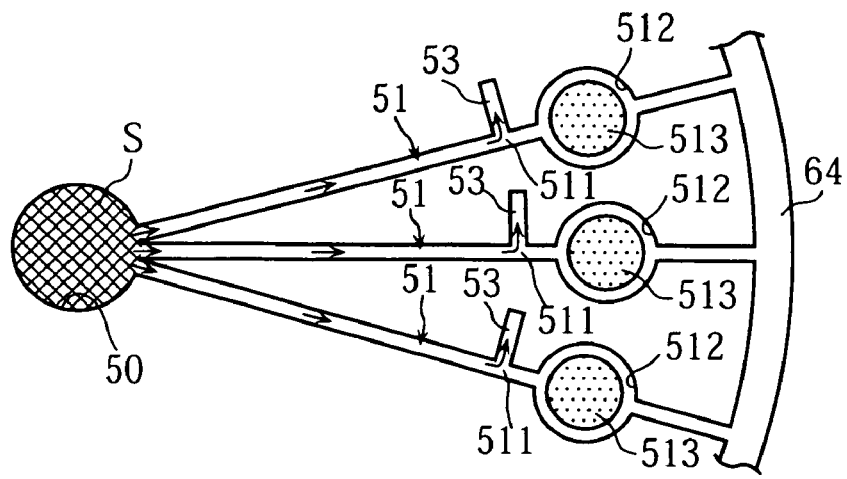
FIGS. 10A-10C are views illustrating how a sample moves through passages.

When the sample fluid S is supplied to the micro device Y1, the sample fluid S moves through the thickness of the separation sheet 8 and reaches the fluid reservoir 50 as expected from FIG. 5A and FIG. 5B. During this movement, solid components in the sample fluid S are removed. If the sample fluid S is blood for example, blood cell components in the blood are removed. While the sample fluid S is supplied, the first and the second gas releasing ports 62, 65 are closed. Therefore, as shown conceptually in FIG. 10A, the sample fluid S is held in the fluid reservoir 50 and will not flow into the passages 51.

The sample fluid S is introduced into the passages 51 by simply making an opening in the sealing members 66 simultaneously. Making an opening in the sealing members 66 is carried out as shown in FIG. 8, by lowering the opening mechanism 41 thereby piercing each of the sealing members 66 by the needles 412, and then raising the opening mechanism 41 thereby pulling out the needles from the sealing members 66. In this operation, openings are made simultaneously in the sealing members 66. The lowering and raising operations of the opening mechanism 41 are made automatically in the analyzer X1 as the user turns on a switch for example.

Figure 10B:
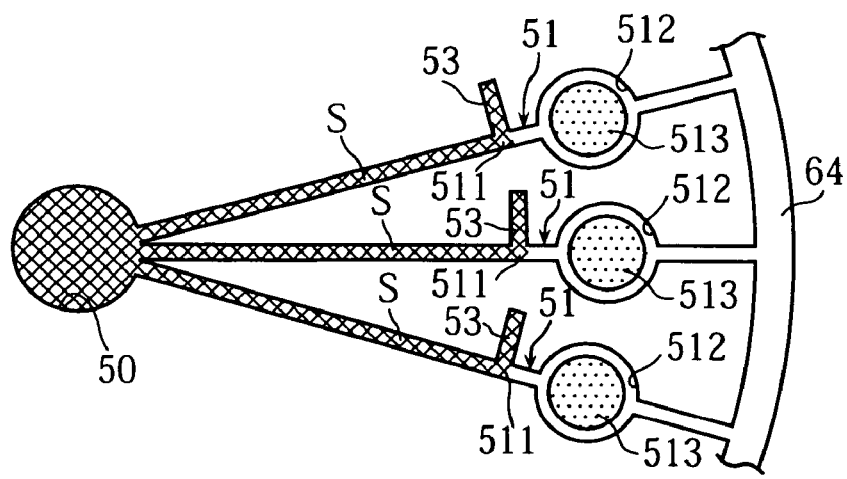

Once the opening is made in the sealing member 66, inside space of the passage 51 communicates with outside via the gas releasing port 62 and the branch passage 53. Therefore, the sample fluid S held in the fluid reservoir 50 now moves inside the passage 51 by capillarity. As indicated by arrows in FIG. 10A, the sample fluid S which has reached the branching region 511 can no longer move beyond the branching region 511 and is introduced into the branch passage 53. This achieves a situation, as shown conceptually in FIG. 10B, in which the sample fluid S is very close to the reactor 512, or the sample fluid S is ready for reaction in the reactor 512.

Then, in order to supply the sample fluid S to the reactor 512, simply, an opening is made in the sealing member 67. Making an opening in the sealing member 67 is carried out as shown in FIG. 9, by lowering the opening mechanism 42 thereby piercing the sealing member 67 by the needle 421, and then raising the opening mechanism 42 thereby pulling out the needle from the sealing member 67. The lowering and raising operations of the opening mechanism 42 are made automatically in the analyzer X1 as the user turns on a switch for example.

Figure 10C:
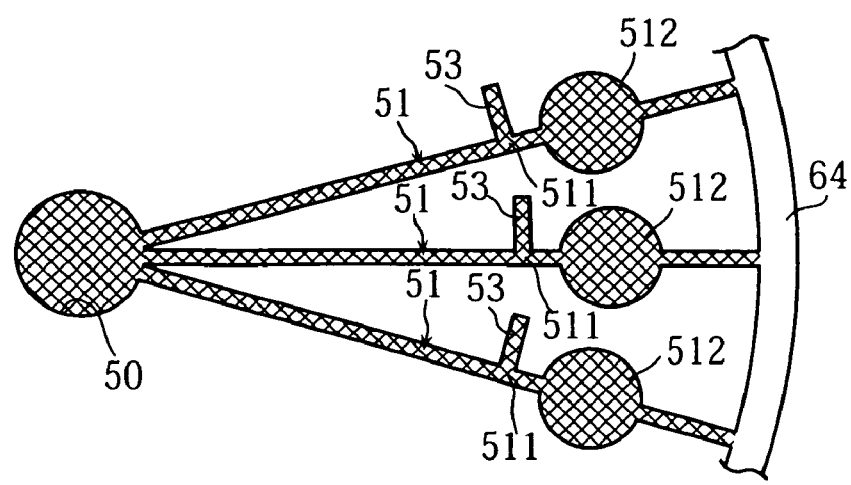

Once the opening is made in the sealing member 67, inside space of the passage 51 communicates with outside via the second gas releasing port 65 and the common passage 64. Therefore, the sample fluid S which has been stopped short of the reactor 512 begins moving again inside the passage 51 by capillarity. As shown in FIG. 10C, the sample fluid S flows beyond the branching region 511 in each passage 51, and thus all of the reactors 512 are supplied with the sample fluid S in a single operation. During this, since the common passage 64 is formed in the cover 6, and the passage 51 is formed in the substrate 5, the sample fluid S that has moved through the passage 51 is appropriately prevented from flowing into the common passage 64, as has been mentioned earlier.

In the reactor 512, the sample fluid dissolves the reagent region 513, and a liquid reaction system is established, causing the sample fluid S to react with the reagent. As a result, a specific colorization occurs for example, in the liquid reaction system in accordance with the amount of target component in the sample, or a specific amount of reactant is produced in accordance with the amount of target component in the sample. This gives the liquid reaction system in the reactor 512 a specific light transparency (light absorbing characteristics) in accordance with the amount of target component in the sample. In a predetermined time duration measured from the supply of the sample to the reactor 512, the light source 2 shown in FIG. 1 and FIG. 2 throws light to the reactor 512, and the amount of light which has passed through is measured by the light receiver 3. The throwing of light by the light source 2 and the light reception by the light receiver 3 is made for each of the reactors 512 in each passage 51 while the mount 1 is being rotated by a predetermined angle. In the analyzer X1, the amounts of light received by the light receiver 3 give the basis for the analysis such as calculation of the concentration level of a target component.

According to the method described above, the sample fluid S is first introduced to a close proximity (in the branching region 511) of the reactor 512, and then the sample fluid S in the branching region 511 is supplied to the reactor 512 by making an opening in the sealing member 67. In other words, it is possible to supply the sample fluid S to all of the reactors 512 in the passages 51 by simply opening a single gas-releasing port. Therefore, only a short time is necessary from the starting of supply of the sample fluid S (piercing the sealing member 67) to the delivery of the sample fluid S to the reactor 512. This leads to decreased inconsistency per passage 51, as well as per measurement (per analyzing article), in terms of the time from starting the supply to the arrival of the sample. As a result, it becomes possible to control the start timing of reactions at the reactors 512, appropriately by an operation of making an opening in the sealing member 67.

The present invention is not limited to the mode of embodiment described above, and may be varied in many ways. For example, the analyzing article according to the present invention may be as shown in FIG. 11 through FIG. 14. It should be noted however, that these figures are conceptual diagrams, showing passages for gas and liquid. Members and components which are identical with those used in the micro device Y1 are identified with the same alpha-numerical codes, and their description will not be repeated.

Figure 11:
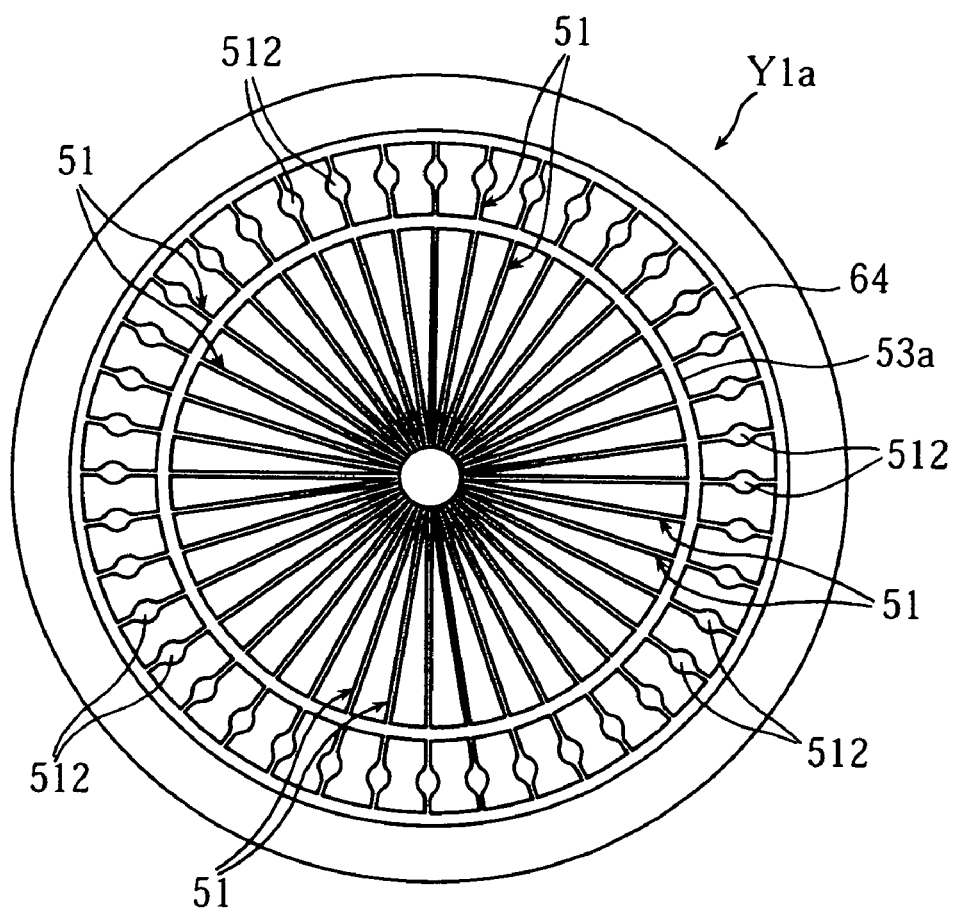
FIG. 11 is a conceptual plan view for describing another analyzing article provided with a common passage.

An analyzing article Y1a in FIG. 11 differs from the analyzing article Y1 described earlier (See FIG. 6) in that passages 51 are interconnected by an additional common passage 53a. The additional common passage 53a communicates with an additional gas releasing port which is out of the sight of the figure. By opening this port, it is possible in all of the passages 51 to introduce the sample short of the reactors 512 simultaneously.

Figure 12:
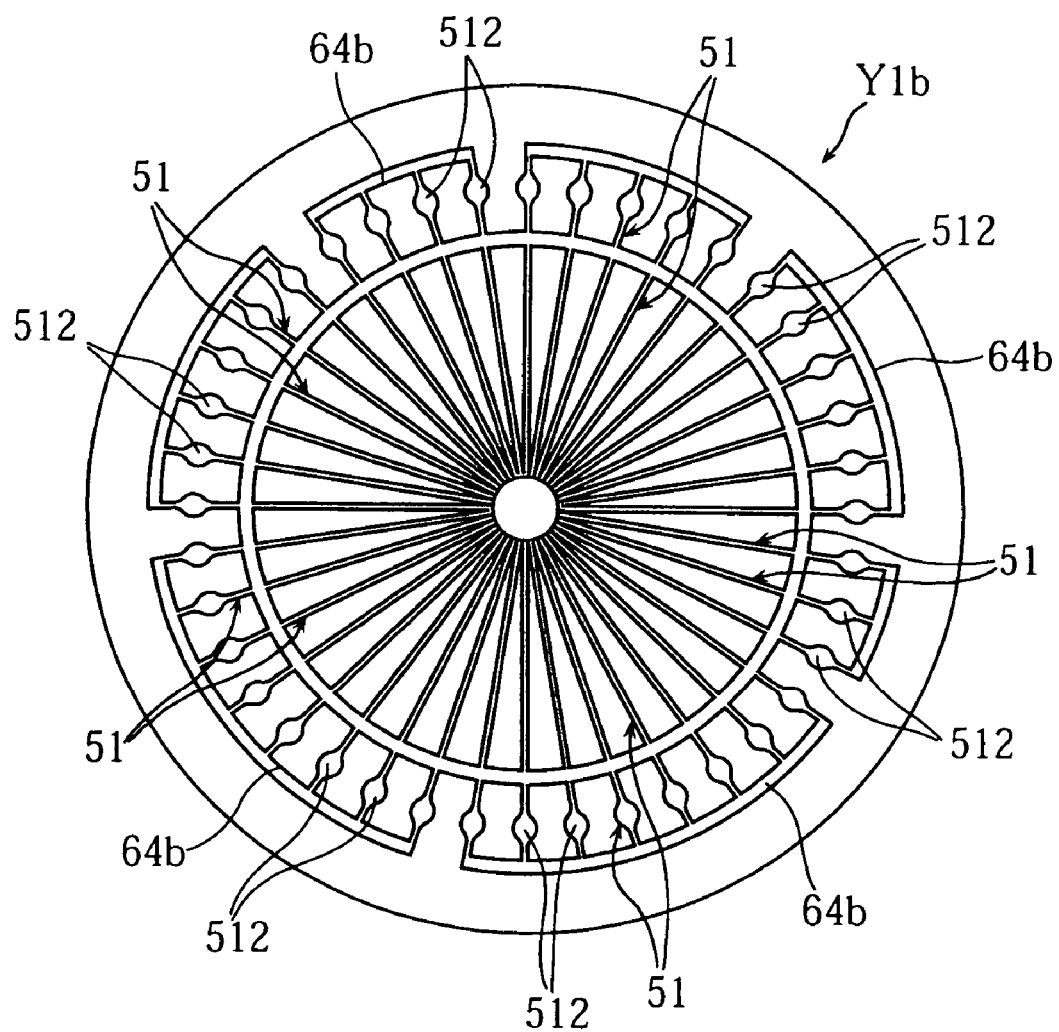
FIG. 12 is a conceptual plan view for describing still another analyzing article provided with a common passage.

The analyzing article Y1b in FIG. 12 has a plurality of common passages 64b. The common passages 64b divide the passages 51 into a plurality of groups. Each common passage 64b communicates with an additional gas releasing port which is out of the sight of the figure. By opening this port, the sample is introduced short of the reactor 512 in all of the passages 51 in the group. As in the analyzing article Y1a described earlier, the analyzing article Y1b also has its passages 51 interconnected by an additional common passage 64b. Therefore, it is possible to move the sample fluid short of the reactors 512 in all of the passages 51. Alternatively, the analyzing article Y1b may have the construction used in the analyzing article Y1 (See FIG. 6), in which each passage 51 is connected with a branch passage which connects with a gas releasing port.

Figure 13:
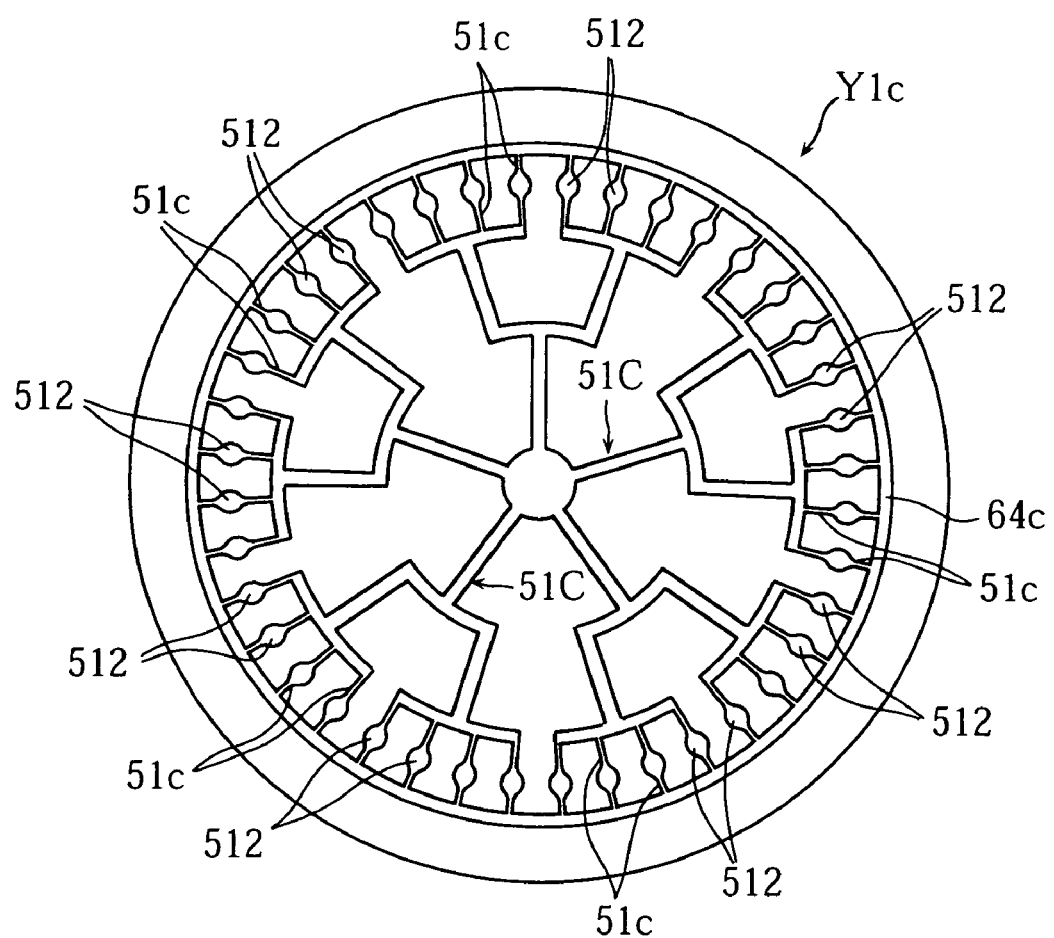
FIG. 13 is a conceptual plan view for describing still another analyzing article provided with a common passage.

An analyzing article Y1c in FIG. 13 is the same as the analyzing article Y1 in that a plurality of reactors 512 are disposed on a circle along the edge of the analyzing article Y1c. A difference however, is that whereas each passage has one reactor 512 in the analyzing article Y1, the passages 51 branch off and each branch 51c has one reactor 512 in the analyzing article Y1c. Each branch 51c communicates with a common passage 64c which leads to a gas releasing port (not illustrated). Therefore, by opening the gas releasing port, it is possible to supply the sample short of the reactors 512 simultaneously.

Figure 14:
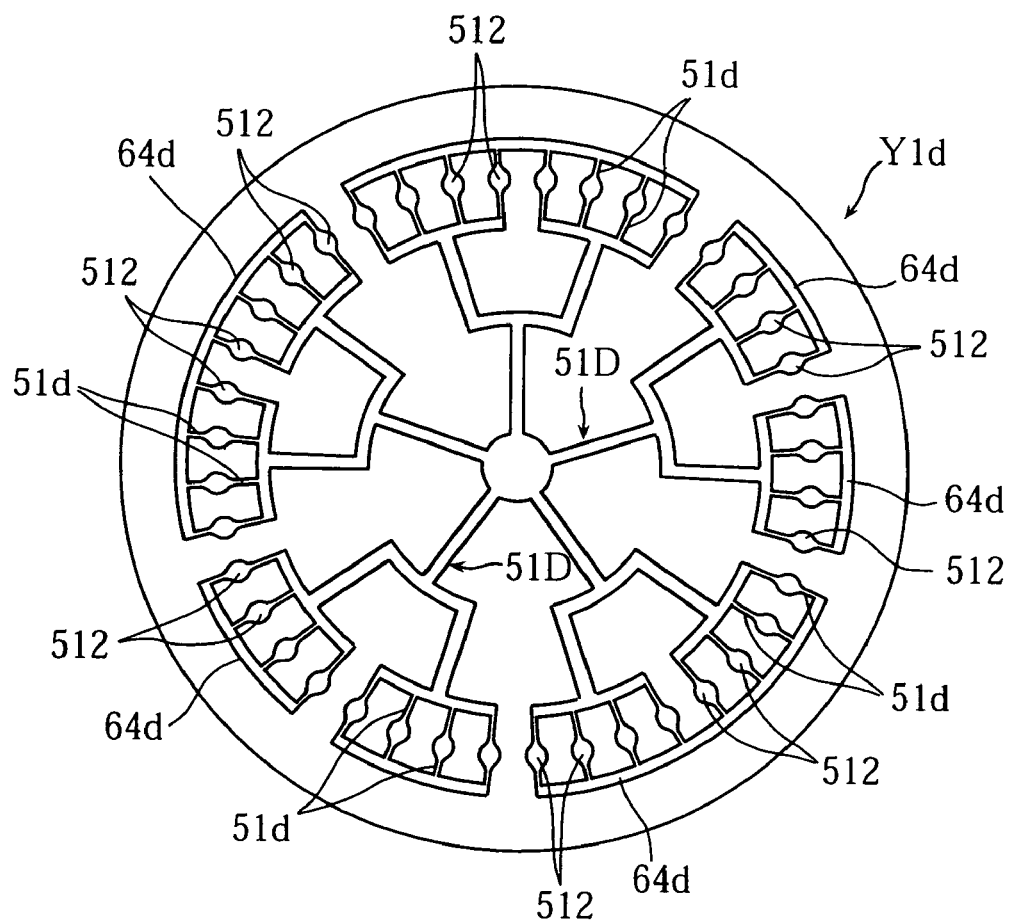
FIG. 14 is a conceptual plan view for describing still another analyzing article provided with a common passage.

An analyzing article Y1d in FIG. 14 has a plurality of common passages 64d, which is essentially the common passage 64c in the analyzing article Y1c (See FIG. 13) divided into a plurality of regions. Specifically, a plurality of passages 51D branch off into a plurality of branches 51d, which are divided into a plurality of groups, and all of the branches 51d in the same group are interconnected by a common passage 64d. In this analyzing article Y1d, it is possible to supply a sample fluid to all of the reactors 512 in the branches 51d in the same group simultaneously.

The analyzing article according to the present invention may not be like a disc, but may also be rectangular as shown in FIG. 15 through FIG. 23 for example.

Figure 15:
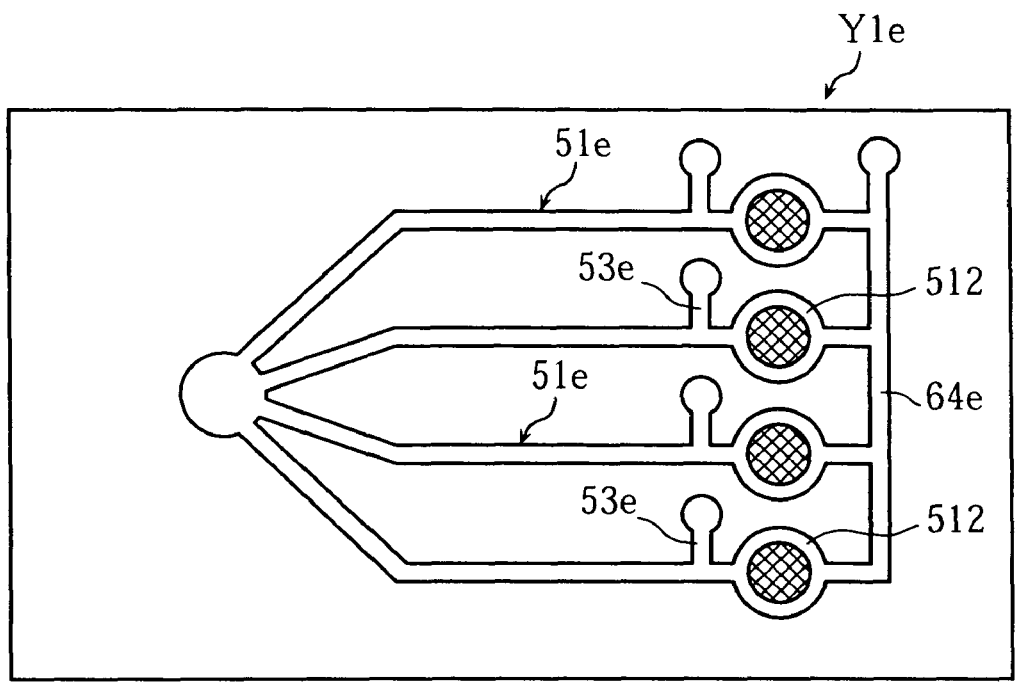
FIG. 15 is a conceptual plan view for describing still another analyzing article provided with a common passage.

An analyzing article Y1e in FIG. 15 is generally rectangular as a whole, and primary portions of passages 51e are parallel to each other. Each passage 51e is, like the passage 51 in the analyzing article Y1 (See FIG. 6), connected with a branch passage 53e at a place short of a reactor 512, and the passage 51e has an end connected with a common passage 64e. Therefore, according to the analyzing article Y1e, it is possible, after moving the sample fluid short of the reactors 512, to introduce the sample fluid to each of the reactors 512 all at once.

Figure 16:
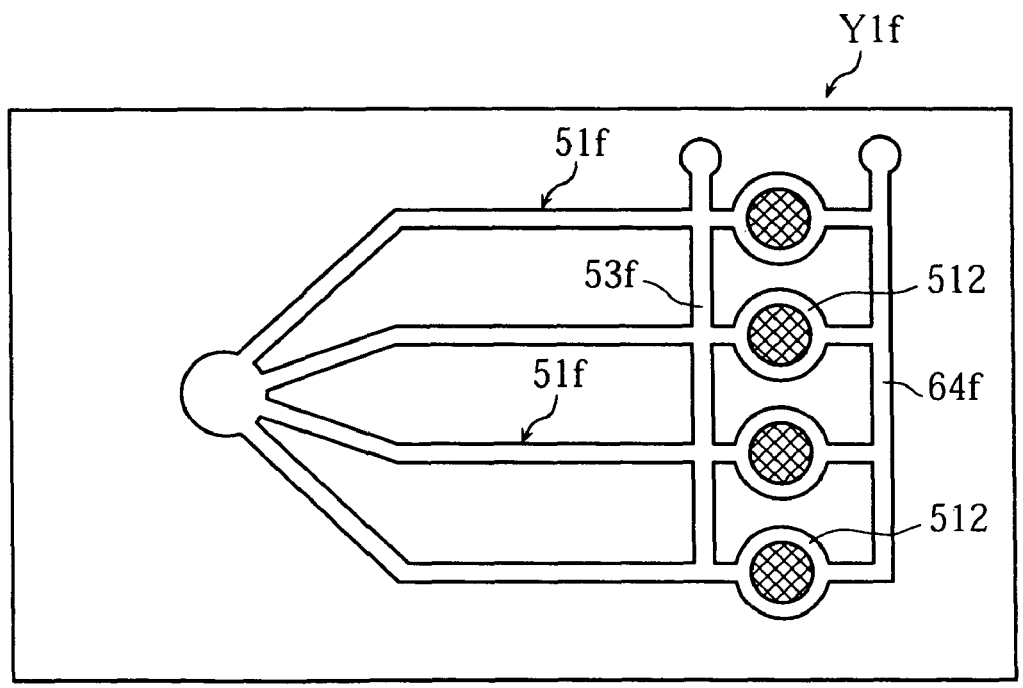
FIG. 16 is a conceptual plan view for describing still another analyzing article provided with a common passage.

An analyzing article Y1f in FIG. 16 is a variation of the analyzing article Y1e (See FIG. 15) in which a plurality of passages 51f are interconnected by an additional common passage 53f. Therefore, according to the analyzing article Y1f, it is possible to supply the sample short of the reactor 512 in each of the passages 51f all at once by establishing communication between the additional common passage 53 with outside.

Figure 17:
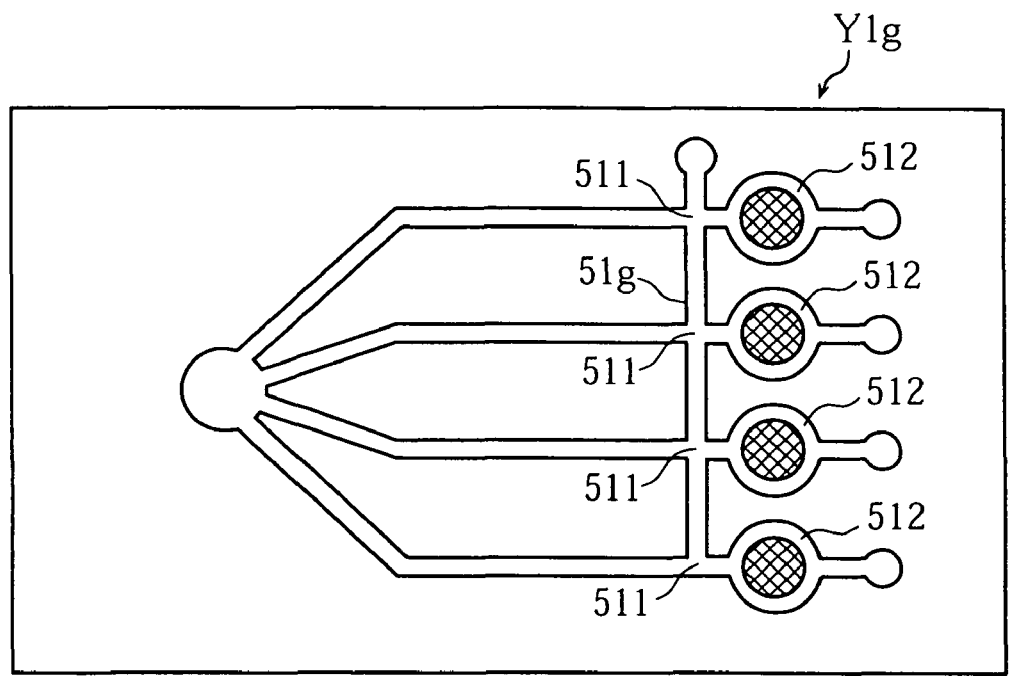
FIG. 17 is a conceptual plan view for describing still another analyzing article provided with a common passage.

In an analyzing article Y1g in FIG. 17, movement of the sample fluid to the branching regions 511 is carried out all together by a common passage 51g, and then supplying of the sample fluid to reactors 512 can be carried out individually.

Figure 18:
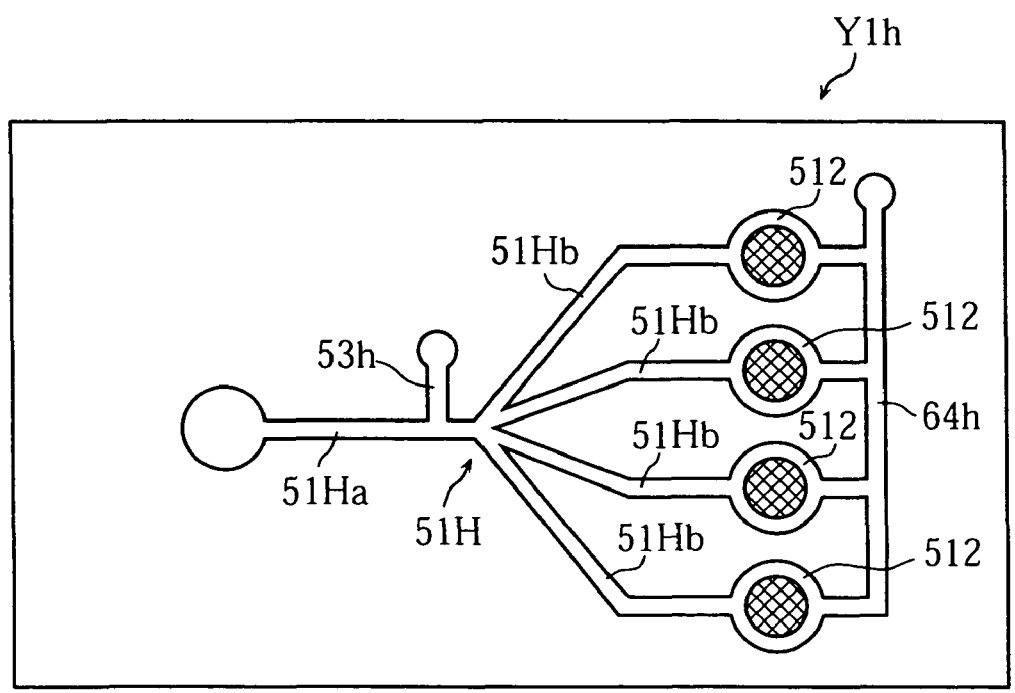
FIG. 18 is a conceptual plan view for describing still another analyzing article provided with a common passage.

An analyzing article Y1h in FIG. 18 includes a passage 51H which has a supply passage 51Ha and a plurality of individual passages 51Hb. The supply passage 51Ha has an end, from which a branch passage 53h extends. In this construction, by establishing communication between the branch passage 53h with outside, the sample fluid moves short of reactors 512, and then by establishing communication between a common passage 64h with outside, the sample fluid is supplied to each of the reactors all at once.

Figure 19:
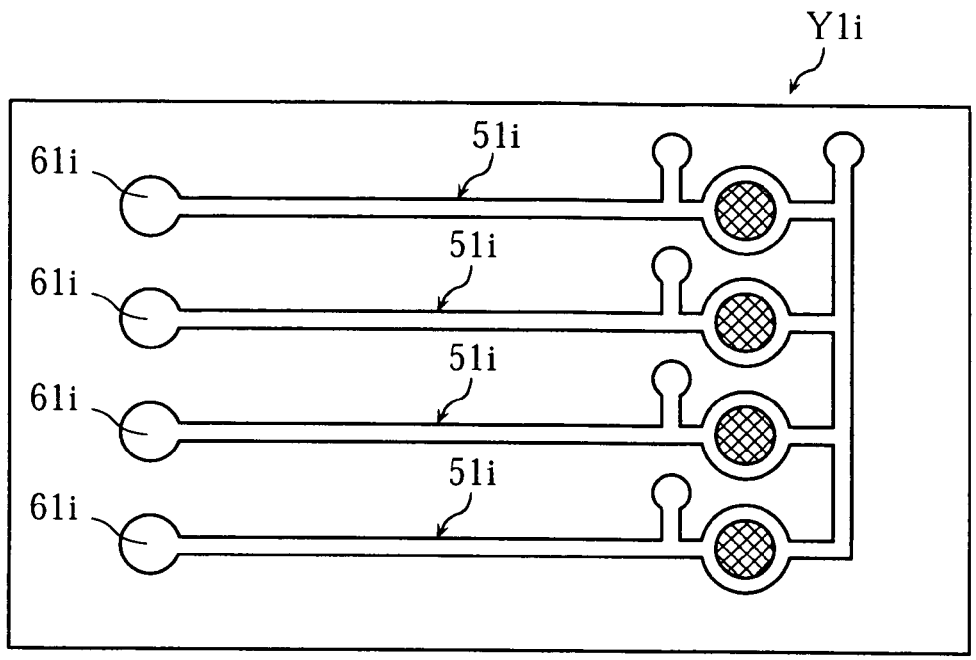
FIG. 19 is a conceptual plan view for describing still another analyzing article provided with a common passage.

An analyzing article Y1i in FIG. 19 is the analyzing article Y1e (See FIG. 15) in which each passage 51i is provided with a sample entrance port 61i. Therefore, according to the analyzing article Y1i, it is possible to introduce the sample fluid individually into each of the passages 51i. Obviously, the passages 51i may be interconnected by an additional common passage in the analyzing article Y1i (See FIG. 16).

Figure 20:
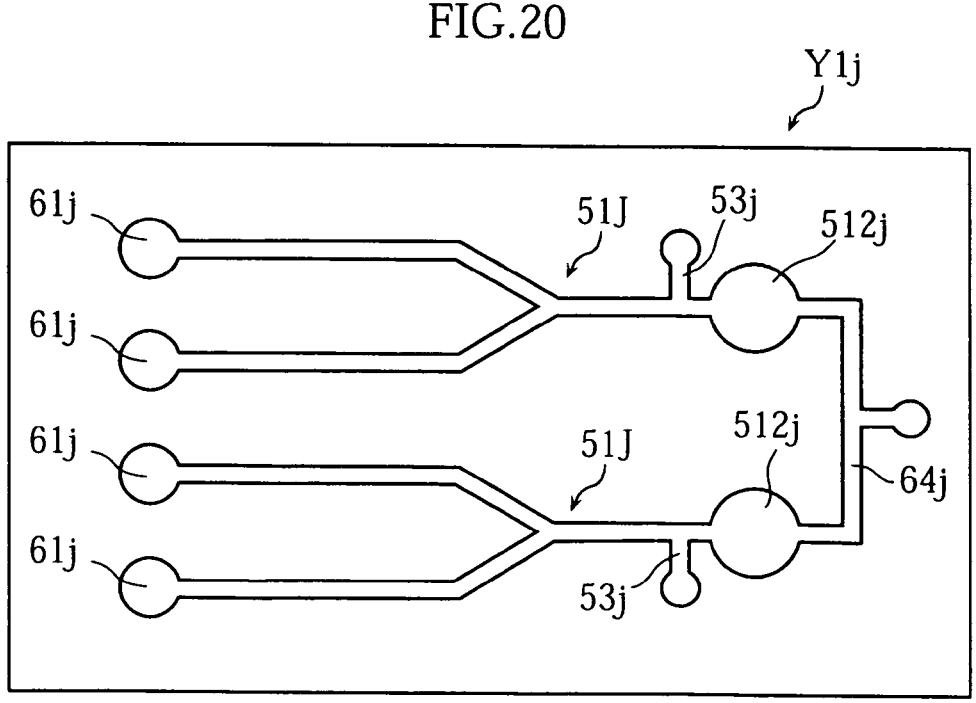
FIG. 20 is a conceptual plan view for describing still another analyzing article provided with a common passage.

An analyzing article Y1j in FIG. 20 includes a plurality (two in the figure) of passages 51J. Each of the passages 51J receives two kinds of fluids (e.g. a sample and a reagent) introduced from two fluid entrance ports respectively, which mix with each other and then move to a measurer 512j. Each passage 51J is connected with a branch passage 53j which branches off at a place short of the measurer 512j. Each passage 51J has an end which is connected to each other by a common passage 64j. Therefore, it is possible to introduce the mixture of the reagent and the sample to all of the measurers 512j in the passages 51J.

Figure 21:
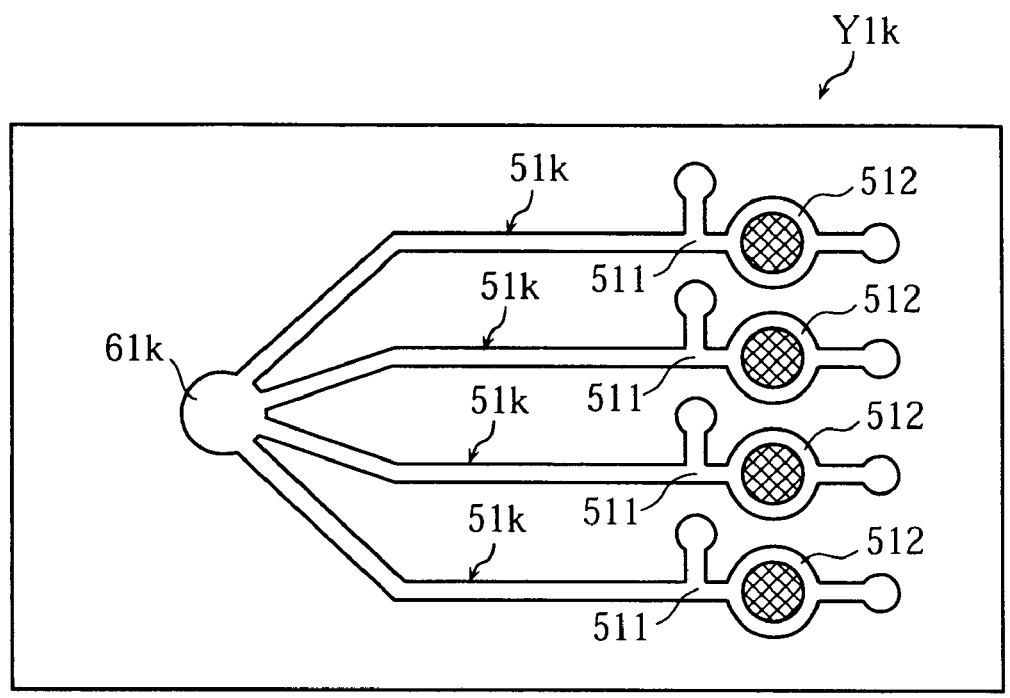
FIG. 21 is a conceptual plan view for describing another analyzing article provided with a plurality of passages.

An analyzing article Y1k in FIG. 21 has one fluid entrance port 61k, with which a plurality of passages 51k are connected. Movement of the sample fluid to branching regions 511 can be made individually, and supply of the sample fluid to reactors 512 can be made individually.

Figure 22:
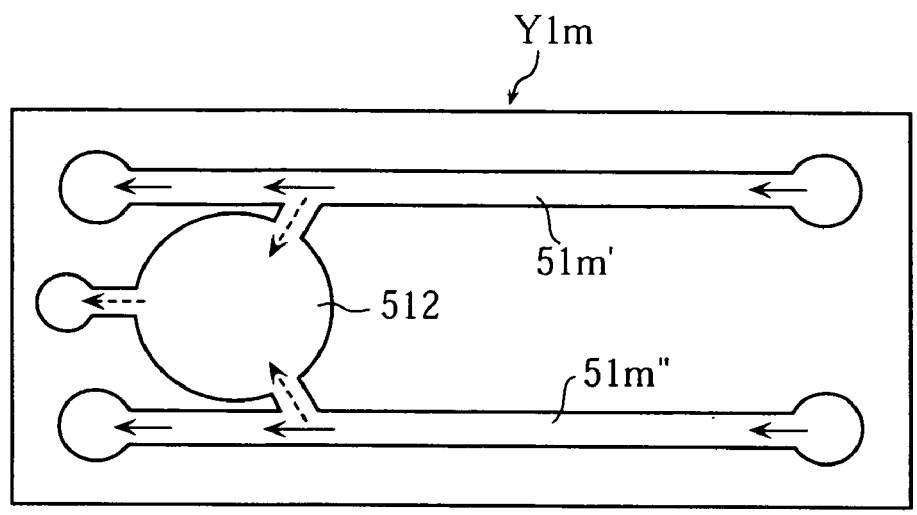
FIG. 22 is a conceptual plan view for describing still another analyzing article provided with a plurality of passages.

An analyzing article Y1m in FIG. 22 is for a reaction system involving three components, such as one sample and two reagents reacting with the sample. A reactor 512 can be supplied from two routes (passages 51m', 51m") with two mobile components (such as a sample and a reagent, or two kinds of reagents) individually and simultaneously. It should be noted here that if the reaction system is to involve three components, the reactor 512 has to be loaded with a reagent or a sample in advance, whereas if the reactions system is to involve only two components, a sample and a reagent should simply be supplied via respective passages 51m', 51m", so there is no need for the reactor 512 to be loaded with a reagent or a sample in advance. Obviously, it is possible to use three or a greater number of routs to supply three or more mobile components individually and simultaneously.

Figure 23:
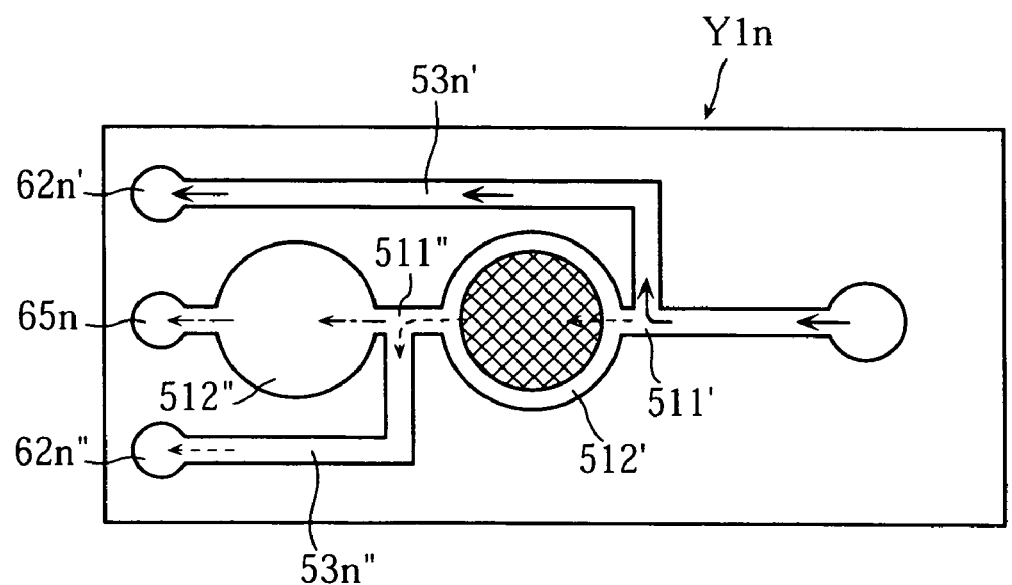
FIG. 23 is a plan view of an analyzing article provided with a plurality of branch passages.

An analyzing article Y1n in FIG. 23 includes a reactor 512' for reaction between a sample and a reagent, and a measurer 512" for measurement. The reactor and the measurer are separated from each other. Components are allowed to react in the reactor 512', and then the target component is moved to the measurer 512" for measurement. Before the reactor 512' are a first branching region 511', and a first branch passage 53n' which extends from the first branching region 511'. On the other hand, there is a second branching region 511" at a place short of the measurer 572", and a second branch passage 53n" extends from the second branching region 511".

In the analyzing article Y1n, by opening a gas releasing port 62n' in the first branch passage 53n' only, the sample is allowed to flow in the first branch passage 53n' as indicated by solid-line arrows in the figure. The flow then stops short of the reactor 512' (at the first branching region 511'), and prevented from entering into the reactor 512'. From this state, by opening a gas releasing port 62n" in the second branch passage 53n" only, the sample is introduced into the reactor 512' as indicated by broken-line arrows in the figure, and the sample flows through the second branch passage 53n", and then stops short of the measurer 512" (at the second branching region 511"). Then, by opening a gas releasing port 62n, the sample in the reactor 512' is introduced into the measurer 512".

Next, a second mode of embodiment of the present invention will be described. It should be noted here that in the drawings referenced in the description, members and components which are identical with those used in the analyzer X1 and the analyzing article (micro device) Y1 according to the first mode of embodiment (See FIG. 1, FIG. 4 and so on.) are identified with the same alpha-numerical codes, and their descriptions will not be repeated.

Figure 24:
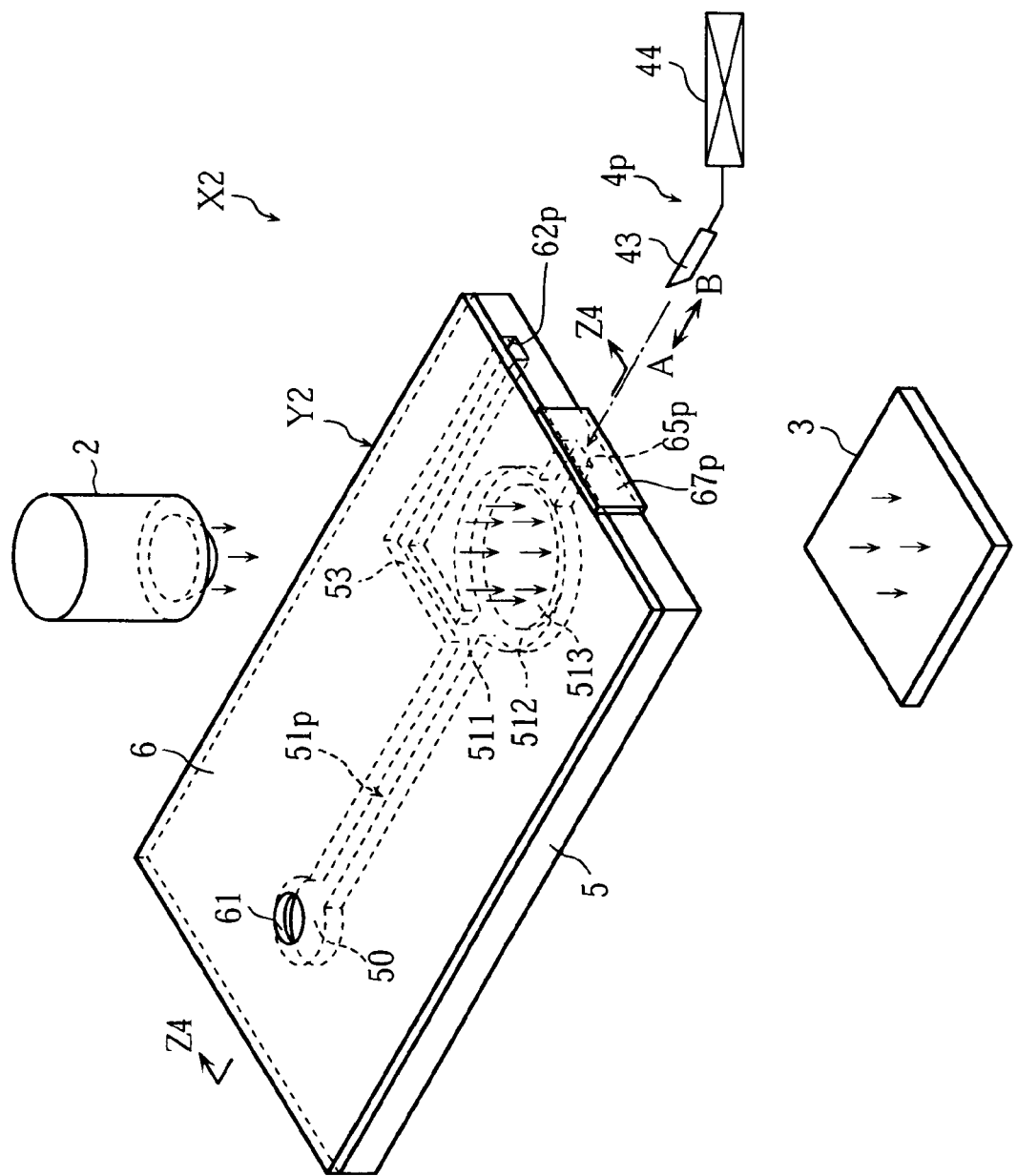
FIG. 24 illustrates a construction of an analyzer and an analyzing article according to a second embodiment of the present invention.

As shown in FIG. 24, an analyzing article Y2 is a micro device as is the previous analyzing article Y1 (See FIG. 4 and so on), but differs from the analyzing article Y1 (See FIG. 4 and so on), in that it includes one passage 51p, and a first and a second gas releasing ports 62p, 65p which are open sideways.

The gas releasing port 65p is sealed by a sealing member 67p which serves as a closer. The sealing member 67p can be formed of a metal such as aluminum, or a resin, and is fixed onto a substrate 5 or a cover 6 with an adhesive or by fusing for example.

On the other hand, the analyzer X2 includes an opener 4p for opening the gas releasing port 65p. The opener 4p has a blade member 43 for cutting the sealing member 67p, and an actuator 44 for reciprocating the blade member 43 in directions indicated by arrows A and B in the figure. In this opener 4p, the blade member 43 is moved by the actuator 44 in the direction A to penetrate the sealing member 67p, and then the blade member 43 is moved by the actuator 44 in the direction B, whereby the sealing member 67p is cut and the gas releasing port 65p is opened. Obviously, there is no limitation to the method of opening the gas releasing port 65p. For example, the blade member 43 may be replaced by a needle member.

Figure 25:
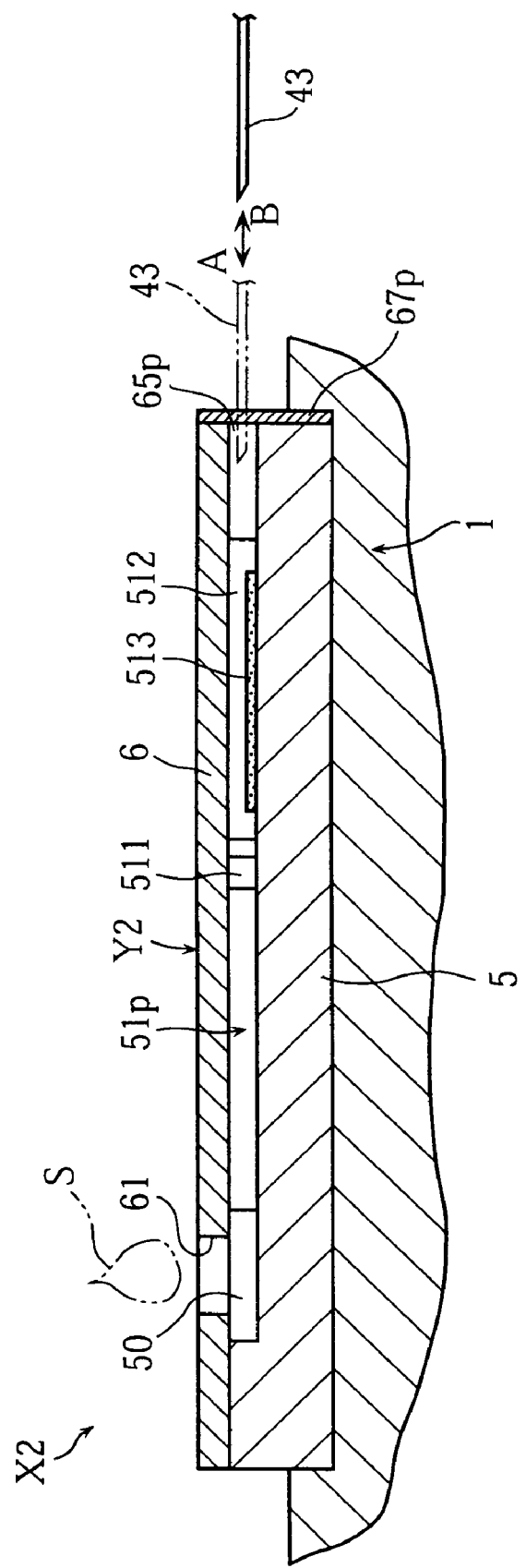
FIG. 25 is a sectional view taken in lines Z4-Z4 in FIG. 24.

When analyzing a sample, first, as shown in FIG. 25, the micro device Y2 has its fluid reservoir 50 supplied with a sample fluid S via a fluid entrance port 61. At this point, as shown clearly in FIG. 24, the gas releasing port 65p is closed and the gas releasing port 62p is opened. Although the supply of the sample fluid S may be made after the analyzing article Y2 has been attached to the analyzer X2, preferably, the sample fluid S is supplied to the analyzing article Y2 in advance, and thereafter the analyzing article Y2 is attached to the analyzer X2.

Figure 26:
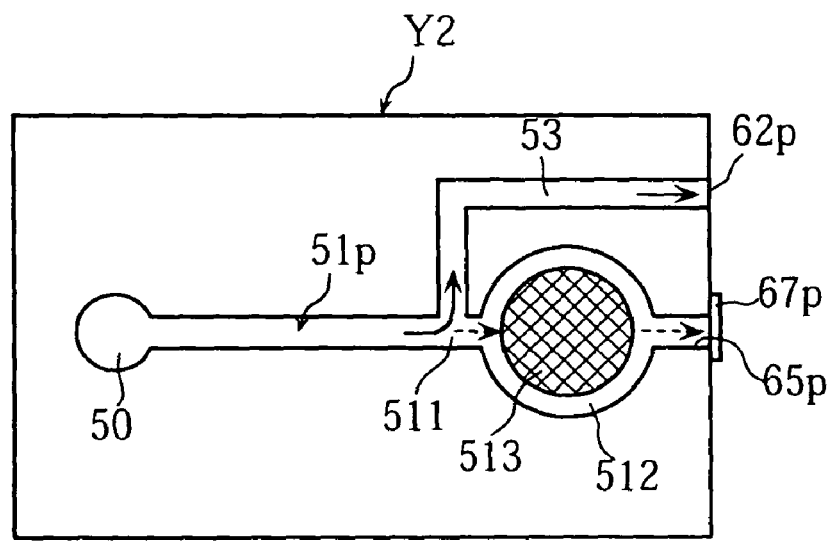
FIG. 26 is a see-through plan view of the micro device in FIG. 25.

Once the sample fluid S is supplied, it moves through the passage 51p by capillarity and reaches a branching region 511. As has been mentioned earlier, the gas releasing port 65p is closed and the gas releasing port 62p is opened in the analyzing article Y2. Therefore, the sample fluid S which has reached the branching region 511 can not go beyond the branching region 511 to reach a reactor 512, and moves through a branch passage 53 as indicated by solid arrows in FIG. 26. This achieves a situation in which the sample fluid S is very close to the reactor 512, or the sample fluid S is ready for reaction in the reactor 512.

Then, in order to supply the sample to the reactor 512, the opener 4p opens the gas releasing port 65p. The opening of the gas releasing port 65p is carried out, as described earlier, by reciprocating the blade member 43 in the directions A and B thereby cutting the sealing member 67p (See FIG. 25). The gas releasing port 65p is opened in this operation, and as indicated by broken-line arrows in FIG. 26, the sample fluid S moves beyond the branching region 511 and is introduced into the reactor 512.

In the reactor 512, the sample reacts with the reagent, which leads to a specific colorization for example, in accordance with the amount of target component in the sample, or a specific amount of reactant is produced in accordance with the amount of target component in the sample. This gives the reactor 512 a specific light transparency (light absorbing characteristics) in accordance with the amount of target component in the sample. In a predetermined time duration measured from the supply of the sample to the reactor 512, a light source 2 shown in FIG. 24 throws light to the reactor 512, and the amount of light passing through is measured by a light receiver 3. The analyzer X2 performs analysis, e.g. calculation of the concentration level of a target component based on the amount of light received by the light receiver 3.

According to the method described above, the sample fluid S is first introduced to a close proximity (in the branching region 511) to the reactor 512, and then the sample fluid S is supplied from the branching region 511 to the reactor 512. Thus, the sample fluid S is supplied upon opening of the gas releasing port 65p when the sealing member 67 has been cut. Therefore, only a short time is necessary from the starting of supply of the sample fluid S (cutting the sealing member 67p) to the delivery of the sample fluid S to the reactor 512. This leads to decreased inconsistency per measurement (per analyzing article), in terms of the time from starting the sample supply to the arrival of the sample. In other words, it becomes possible to control the start timing of reactions at the reactor 512, appropriately by a cutting operation of the sealing member 67p, and as a result, it becomes possible to give a consistent reaction time to every analyzing article Y2, and to decrease measuring errors.

In order to achieve these advantages, it is simply necessary to provide branch passages 53 in the analyzing article Y2, and control open/close status of the gas releasing port 65p. Compared with an analyzing article which incorporates a micro pump, valves and so on, the analyzing article Y2 has a simpler construction. Thus, the analyzing article Y2 can be manufactured without difficulties in terms of manufacturing techniques, and offers an advantage in manufacturing cost. As a result, it becomes possible to supply the analyzing article Y2 which is capable of controlling the reaction timing, at a low price, and it becomes possible to make use of the reaction start timing controlling function in disposable analyzing articles without difficulties.

Obviously, the present invention is not limited to the modes of embodiment described above, and can be varied in many ways. For example, the sealing member 67p may be peeled to open the gas releasing port 65p. The formation and the sealing of a gas releasing port in advance is not an absolute necessity; i.e. an opening which serves as a gas releasing port may be made in the substrate or the cover by the opener after the analyzing article has been attached to the analyzer. Further, a number of different methods can be used for opening and closing gas releasing port in the passages, as will be described hereinafter with reference to FIG. 27-FIG. 31.

Figure 27:
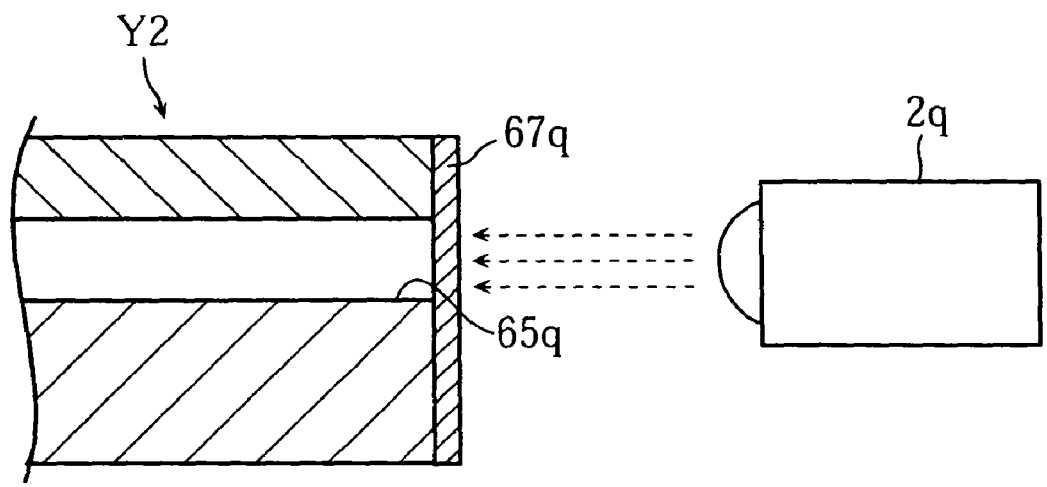
FIG. 27 is a sectional view of a primary portion, for describing another method of opening and closing a gas releasing port of a passage.

FIG. 27 shows an example, in which energy is given to a sealing member 67q thereby melting or deforming the sealing member 67q to open a gas releasing port 65q. The energy can be provided by a light source 2q (e.g. a laser). The energy may alternatively be provided by an ultrasonic wave generator or a heater.

Figure 28A:
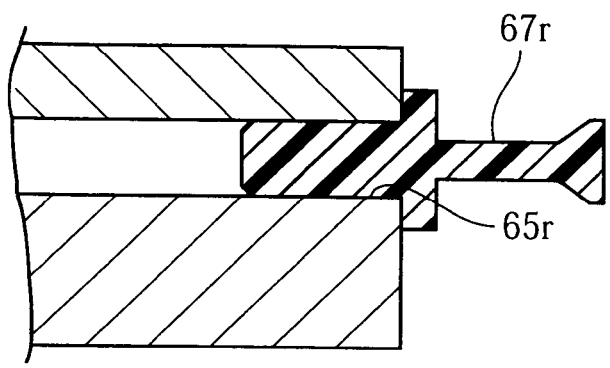
FIG. 28A and FIG. 28B are sectional views of a primary portion, for describing still another method of opening and closing a gas releasing port of a passage.
Figure 28B:
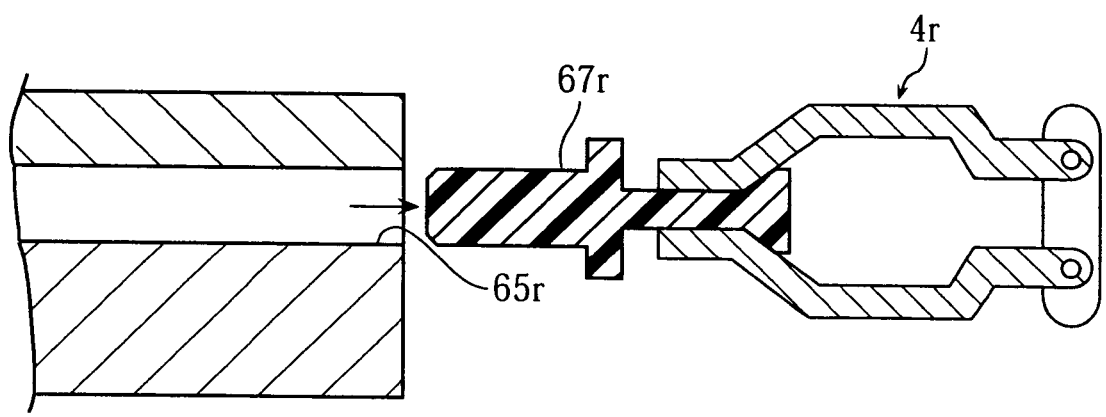

FIG. 28A and FIG. 28B show an example, in which a plug 67r serving as a closer is attached to or detached from a gas releasing port 65r thereby opening and closing the gas releasing port 65r. In this example, the plug 67r is attached to the gas releasing port 65r as shown in FIG. 28A, in order to close the gas releasing port 65r while the sample is being introduced into a branch passage 53 (See FIG. 26 and so on). On the other hand, when the sample is supplied to a reactor 512 (See FIG. 26 and so on), the plug 67r is detached from the gas releasing port 65r as shown in FIG. 28B, in order to open the gas releasing port 65r. The attaching and detaching of the plug 67r is performed by an opener provided in the analyzer (The figure shows a clamp mechanism 4r as an example).

Figure 29A:
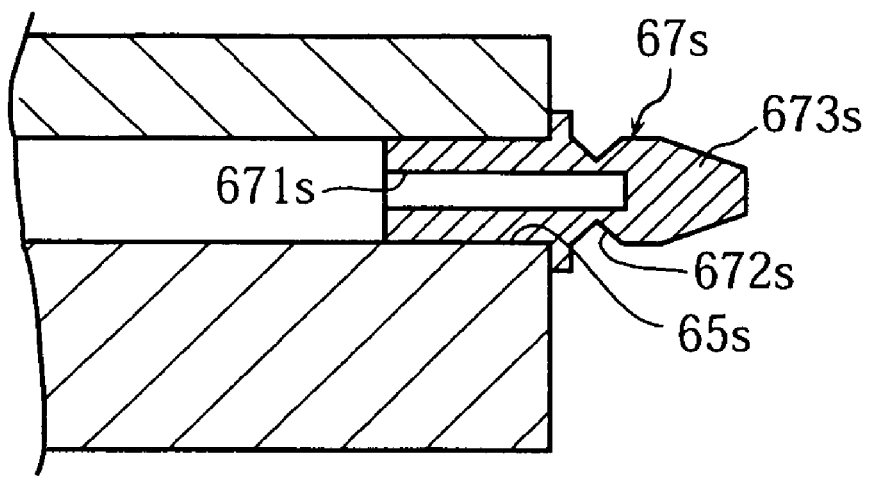
FIG. 29A and FIG. 29B are sectional views of a primary portion, for describing still another method of opening and closing a gas releasing port of a passage.
Figure 29B:
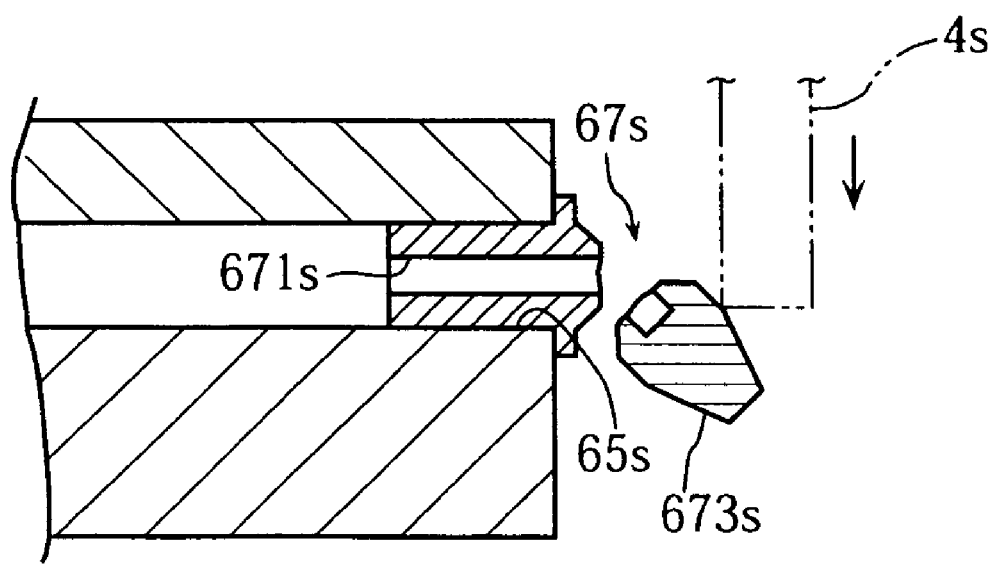

FIG. 29A and FIG. 29B show an example, in which a plug 67s serving as a closer is attached to a gas releasing port 65s. The gas releasing port 65s is opened by cutting an end of the plug 67s. As shown in FIG. 29A, the plug 67s is formed with an inner space 671s and therefore is hollow. The space 671s has a closed rear end and an open front end. A cutout 672s is formed at a tip portion of the space 671s, and by using this cutout 672s, a tip 673s can be easily cut off as shown in FIG. 29B. In this construction, cutting off the tip 673s establishes communication between the space 671s and the gas releasing port 65s, thereby opening the gas releasing port 65s. Therefore, the tip 673s is simply cut off when supplying the sample to a reactor 512 (See FIG. 26 and so on). The cutting operation of the tip 673s is carried out by a hitting mechanism 4s. The hitting mechanism 4s includes a hammer for example, which is capable of hitting the tip 673s.

Figure 30A:
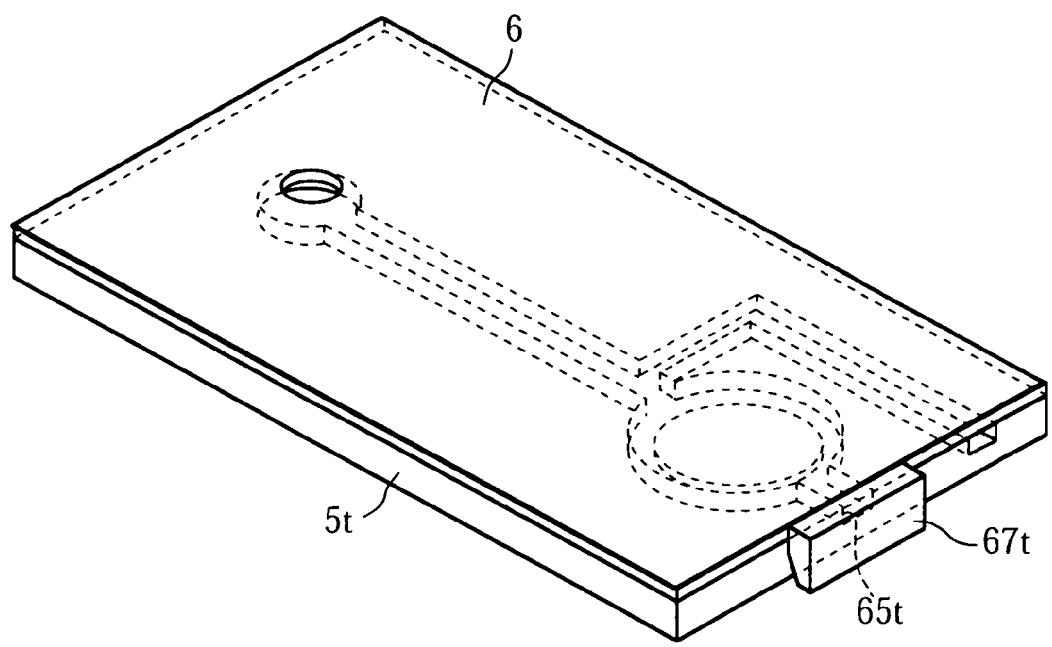
FIG. 30A is an overall perspective view of an analyzing article for describing still another method of opening and closing a gas releasing port of a passage.
Figure 30B:
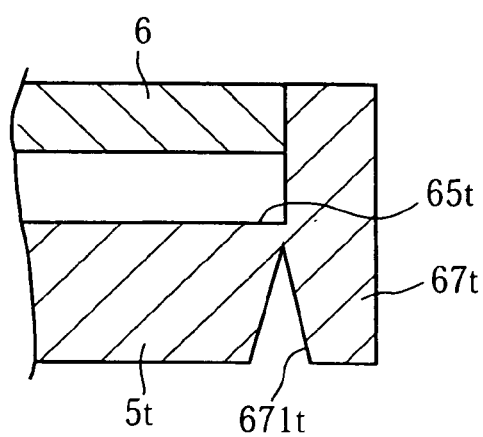
FIG. 30B is a sectional view of a primary portion of the analyzing article in FIG. 30A.

FIG. 30A and FIG. 30B show an example, in which a cut-off tab 67t serving as a closer is cut off to open a gas releasing port 65t. The cut-off tab 67t is formed at an end of a substrate 5t integrally with the substrate 5t. A cutout 671t is formed so that the tab is cut off from the substrate 5t by an external force. The external force is supplied from a hammer for example, as in the previous example.

Figure 31A:
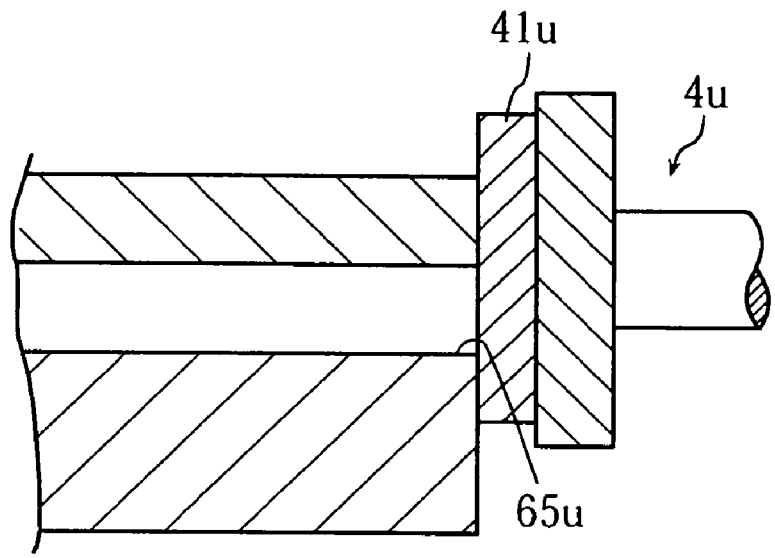
FIG. 31A and FIG. 31B are sectional views of a primary portion, for describing still another method of opening and closing a gas releasing port of a passage.
Figure 31B:
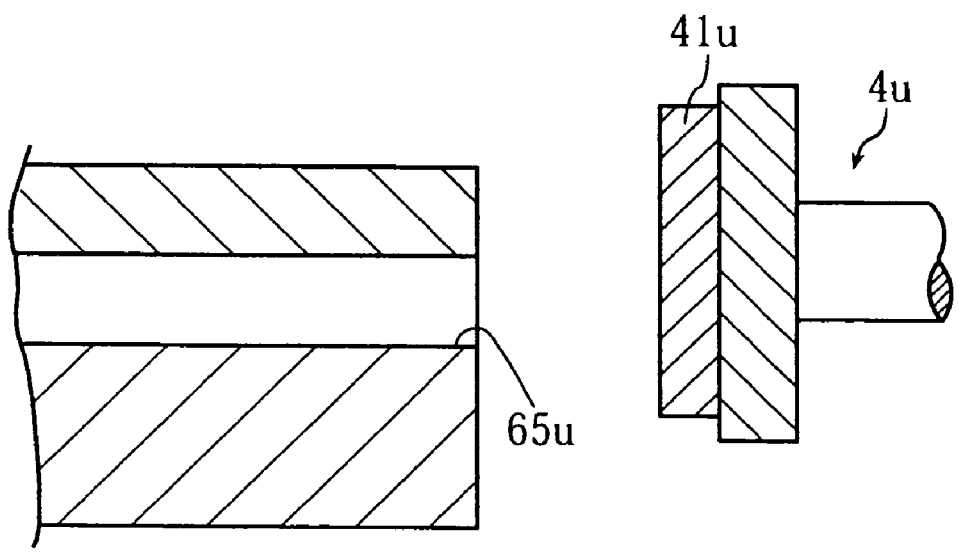

FIG. 31A and FIG. 31B show an example, in which a gas releasing port 65u is opened and closed without a closer. In this example, the analyzer is provided with a closing head 4u, and a selection can be made between a state in which the closing head is fitted thereby closing the gas releasing port 65u and a state in which the closing head 4u is unfitted thereby opening the gas releasing port 65u. In order to assure reliable closure of the gas releasing port 65t when the gas releasing port 65u must be closed, the closing head is preferably provided by a sealing member 41u made of rubber for example, and is disposed at a place from which the gas releasing port 65u is sealable.

Next, a third mode of embodiment of the present invention will be described. It should be noted here that in the drawings referenced in describing the present mode of embodiment, members and components which are identical with those used in the analyzers X1, X2 and the analyzing articles (micro device) Y1, Y2 according to the first and the second mode of embodiments (See FIG. 1, FIG. 4, FIG. 24 and so on) are identified with the same alpha-numerical codes and their descriptions will not be repeated.

Figure 32:
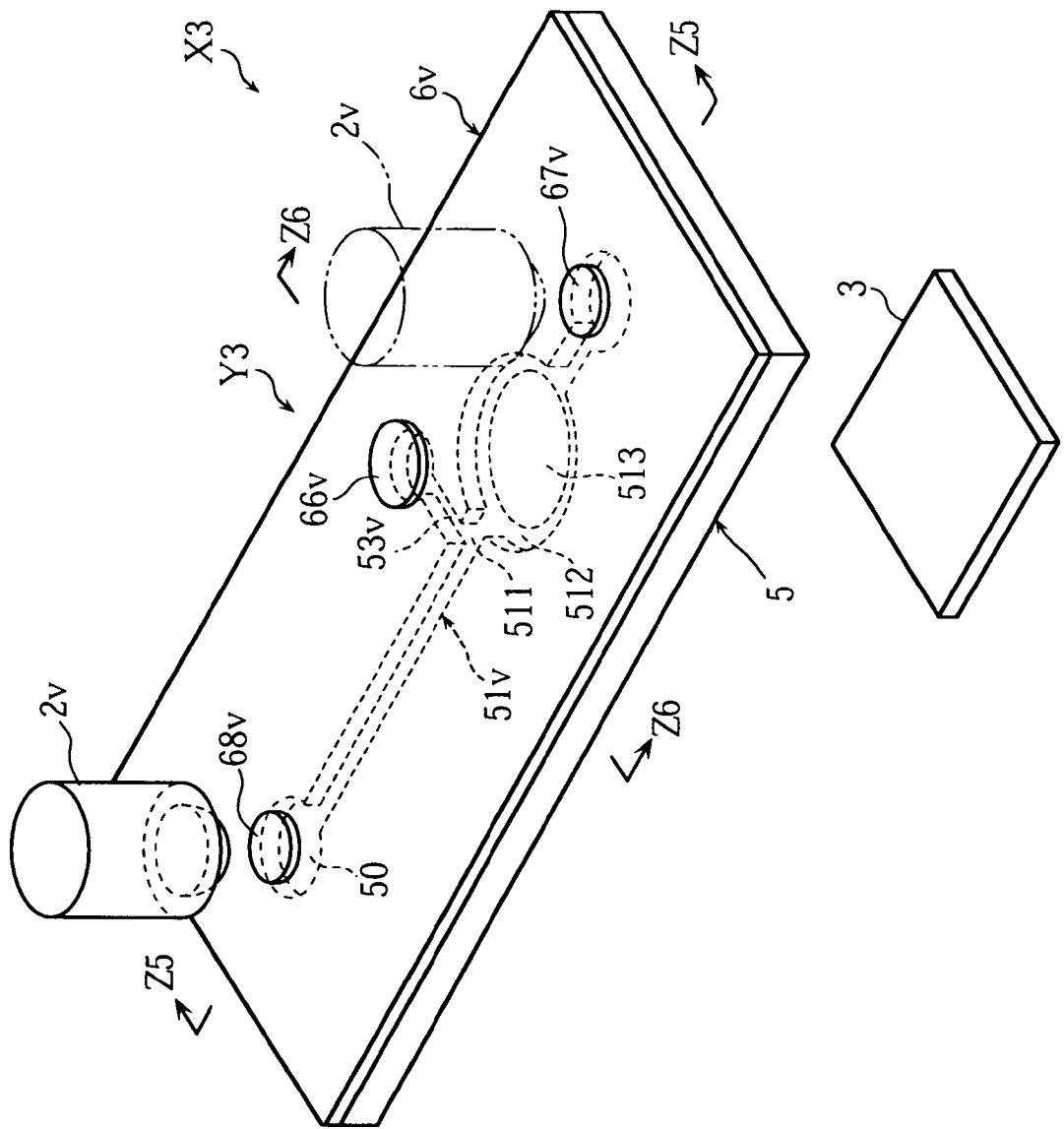
FIG. 32 illustrates a construction of an analyzer and an analyzing article according to a third embodiment of the present invention.
Figure 33:
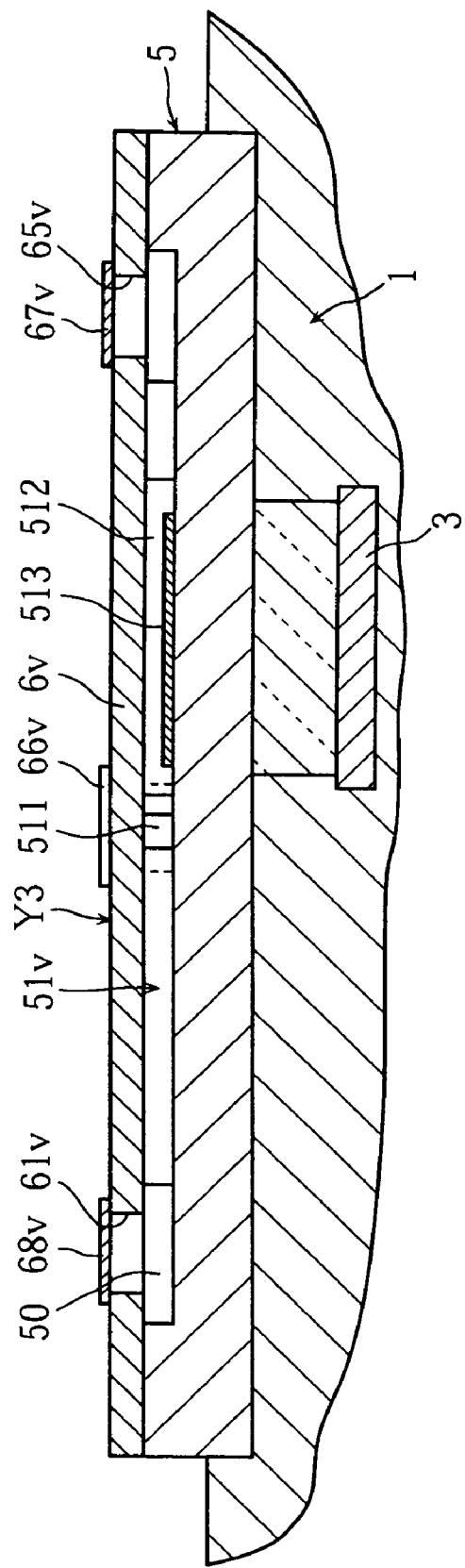
FIG. 33 is a sectional view taken in lines Z5-Z5 in FIG. 32.
Figure 34:
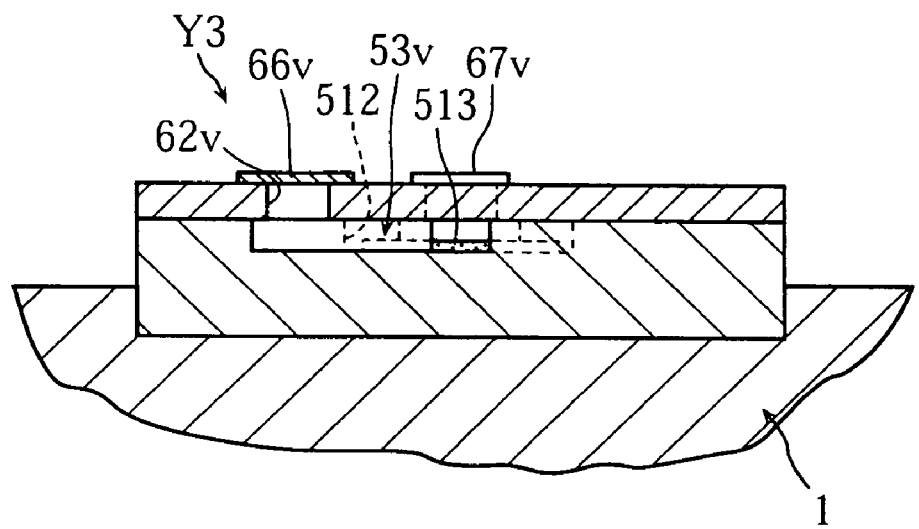
FIG. 34 is a sectional view taken in lines Z6-Z6 in FIG. 32.

As shown in FIG. 32 through FIG. 34, an analyzing article Y3 is essentially the same as the analyzing article Y2 according to the second mode of embodiment. In the analyzing article Y3 however, a cover 6v has a sample fluid entrance port 61v, and gas releasing ports 62v, 65v. The sample fluid entrance port 61v and the gas releasing ports 62v, 65v are closed by sealing members 66v, 67v, 68v respectively, sealing the inside of passage 51v, reducing unwanted exposure of a reagent region 513 to moisture for example.

Each of the sealing members 66v-68v absorb light and the region which has absorbed light melts to form an opening. Formation of the opening establishes communication between inside and outside of the passage 51v. The sealing members 66v-68v are provided by, e.g. a thermoplastic resin which is colored by a colorant dispensed in the resin, and has a thickness of 5-100 μm. Such sealing members 66v-68v are fixed to the cover 6v with an adhesive or by fusion.

The thermoplastic resin preferably has a melting point not higher than 100° C., and provided by e.g. ethylene vinyl acetate copolymer. On the other hand, the colorant can be selected from a number of known coloring products in accordance with the wavelength of the light to be thrown to the sealing members 66v-68v. For example, if the sealing members 66v-68v receive a red light, then a green or black colorant is used. The green colorant can be provided typically by copper phthalocyanine colors, cobalt green ($CoO.Al_2O_3.Cr_2O_3$), and titanium-cobalt green ($TiO_2.CoO.NiOAnO$). The black colorant can be provided typically by carbon dyestuff such as carbon black (C), Copper-Chromium black ($CuO.Cr_2O_3$) and copper-iron black ($CuO.Fe_2O_3$).

The sealing members 66v-68v may contain fillers for purposes of ensured heat storing capacity and increased strength. The filler used for heat storage includes metal particles and glass particles. The filler used for increased strength may be selected from a variety of known materials. Alternatively or in addition to the fillers, use may be made for a mesh material for heat storage and strength.

Figure 35:
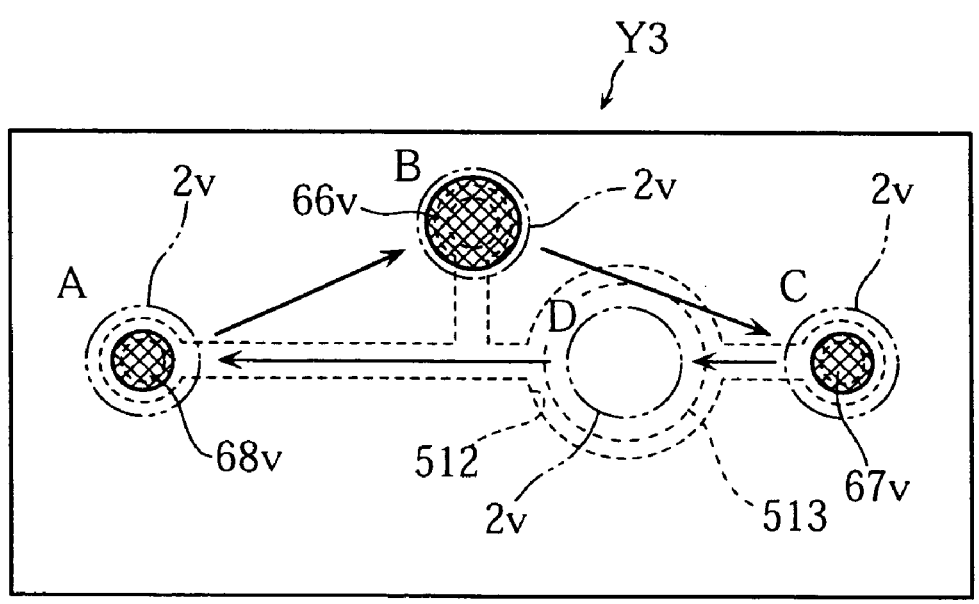
FIG. 35 is a see-through plan view of the analyzing article for describing a transport route for a light source.

On the other hand, the analyzer X3 is essentially the same as the analyzer X2 according to the second mode of embodiment. A difference, however, is that a light source 2v shown in FIG. 32 is capable of throwing light not only to a reactor 512 but also to the sealing members 66v-68v. Specifically, as shown in FIG. 35, the light source 2v is movable between positions A-C above the respective sealing members 66v-68v, as well as to a position D which is above the reactor 512. Alternatively however, the sealing members 66v-68v may be given light from a separate light source which is different from the light source that gives light to the reactor 512. Or still alternatively, each of the sealing members 512 may have an individual light source.

The light source 2v is preferably provided by a laser diode, which enables to make an opening or analysis with a small amount of electricity. Alternatively to the laser diode, the light source 2v may be provided by a light emitting diode, a halogen lamp, a xenon lamp, a tungsten lamp and so on. It should be noted however, that if the light from the light source has a wide range of wavelength and a certain level of intensity (composite light), then the light from the light source $2v$ may be filtered so that the light has a specific wavelength to be applied to the sealing members $66v$-$68v$ and the reactor $512$.

Figure 36A:
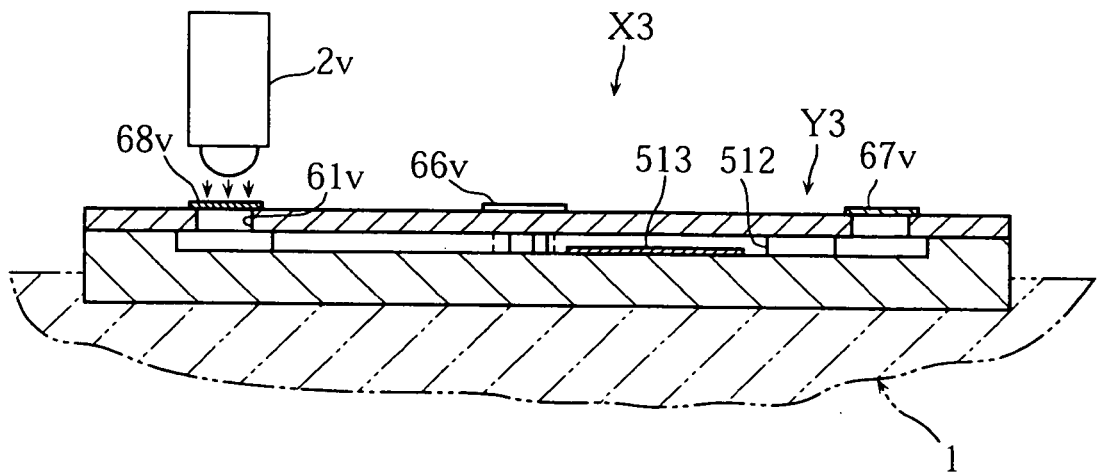
FIG. 36A is a sectional view for describing an opening operation of a sample entrance port.
Figure 36B:
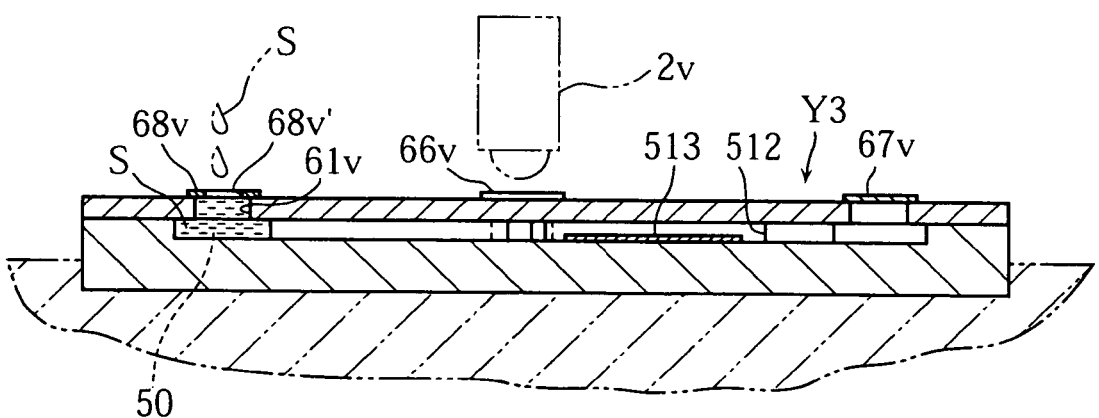
FIG. 36B is a sectional view for describing a sample introducing operation and status.

When analyzing a sample, first, as shown in FIG. 36A, an analyzing article Y3 is attached to a mount 1 in an analyzer X3. As described earlier, the analyzing article Y3 has its fluid entrance port $61v$ closed by the sealing member $68v$, and therefore the sample cannot be introduced under this state. Thus, as shown in FIG. 36B, an opening $68v'$ must be formed in the sealing member $68v$ in order to open the fluid entrance port $61v$. In order to achieve this, as shown in FIG. 35 and FIG. 36A, the light source $2v$ is moved to the position A above the sealing member $68v$ and a light is thrown to the sealing member $68v$ from the light source $2v$ of the analyzer X3. If the light source $2v$ is provided by a laser diode, the laser beam is applied to the sealing member $68v$ in accordance with predetermined conditions involving laser beam wavelength characteristics, composition and thickness of the sealing member $68v$ and so on. Typically however, the laser beam is applied onto a diameter of 50-300 μm, at an output level of 15-50 mW for a time duration of 0.5-10 seconds.

Figure 36C:
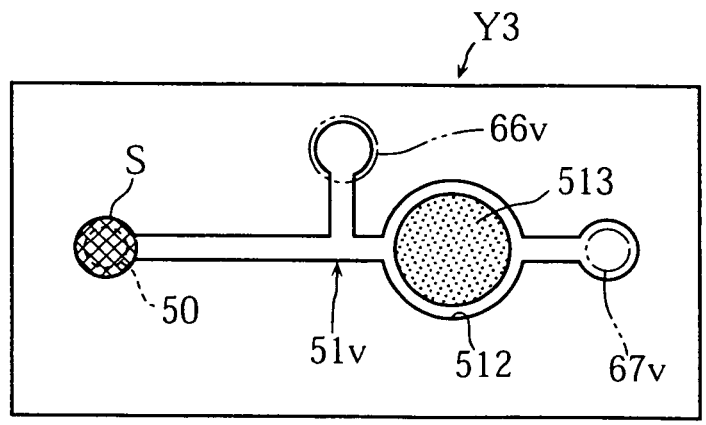
FIG. 36C is a plan view for describing the sample introduction status.

Once the opening $68v'$ has been formed in the sealing member $68v$ as shown in FIG. 36B, a sample fluid S is supplied to a fluid reservoir 50 via the opening $68'$ and the fluid entrance port $61v$ as shown in FIG. 36B and FIG. 36C. Note that the cross-hatching in FIG. 36C represents the sample fluid S.

Figure 37A:
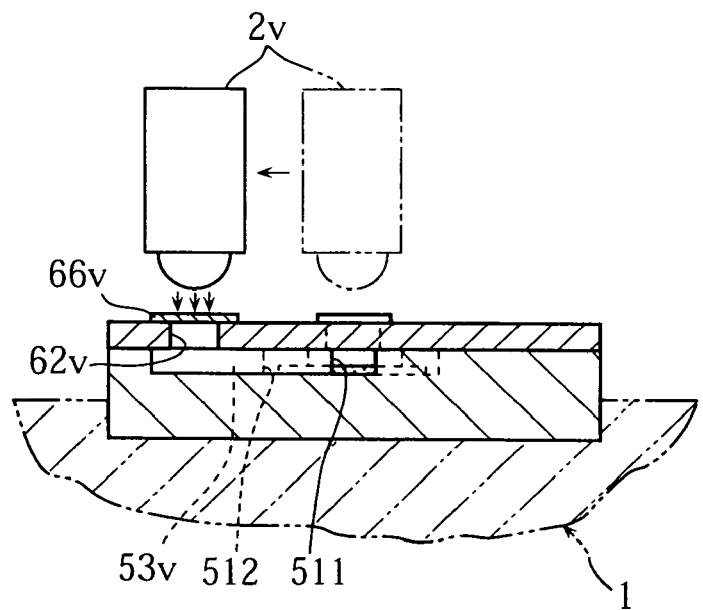
FIG. 37A is a sectional view for describing an opening operation of a gas releasing port.
Figure 37B:
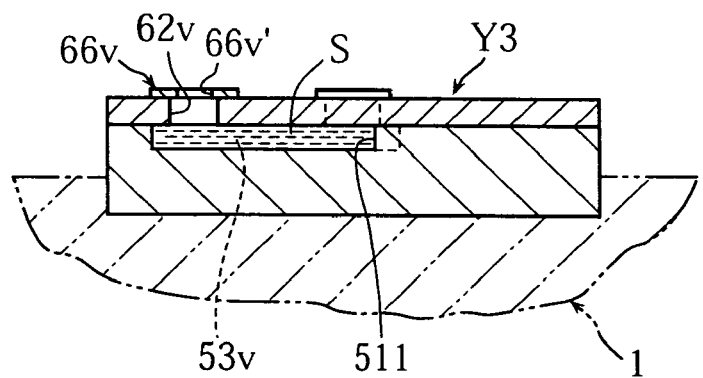
FIG. 37B and FIG. 37C are a sectional view and a plan view respectively for describing a sample introducing status.
Figure 37C:
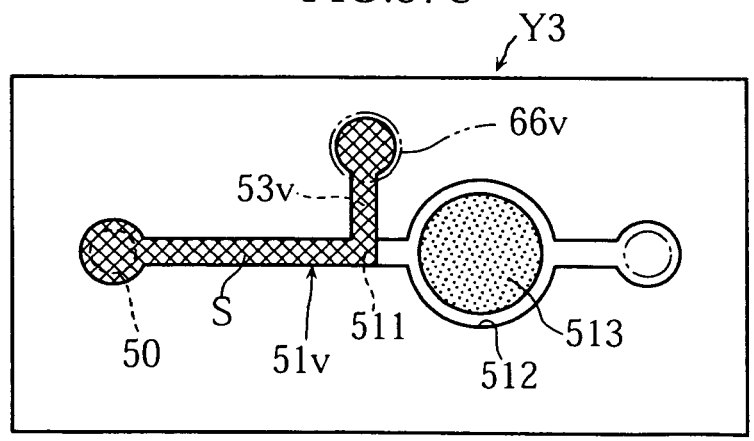

Next, as shown in FIG. 37, the light source $2v$ is moved to above the sealing member $66v$ and the light is thrown to the sealing member $66v$ from the light source $2v$. As shown in FIG. 37B, an opening $66v'$ is formed in the sealing member $66v$ in this operation, which opens the gas releasing port $62v$. Once the gas releasing port $62v$ is open, capillarity occurs in a passage $51v$, to the branching region 511 and in a branch passage 53, allowing the sample fluid S in the fluid reservoir 50 to move to the branching region 511. As has been mentioned earlier, the analyzing article Y3 has its gas releasing port $65v$ closed. Therefore, the sample fluid S which has reached the branching region 511 can not go beyond the branching region 511 to reach the reactor 512, and thus moves to the branch passage 53. This achieves a situation, as shown in FIG. 37B and FIG. 37C, in which the sample fluid S is very close to the reactor 512, or the sample fluid S is ready for reaction with a reagent contained in a reagent region 513, in the reactor 512. It should be noted here that if formation of the opening $68'$ (See FIG. 36B) does not introduce a sufficient amount of the sample fluid S, then as shown in FIG. 37B, an opening $66v'$ may be made before the introduction of the sample fluid S.

Figure 38A:
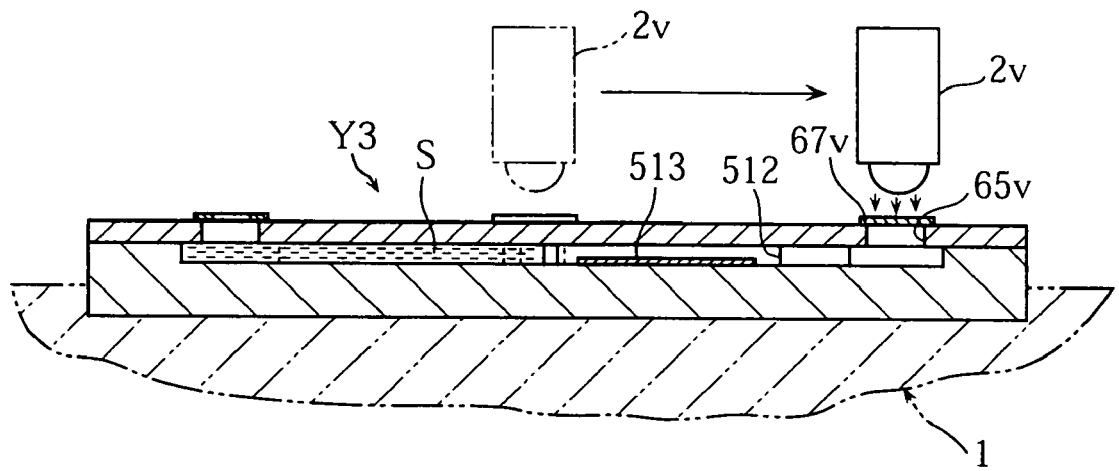
FIG. 38A is a sectional view for describing an opening operation of a gas releasing port.
Figure 38B:
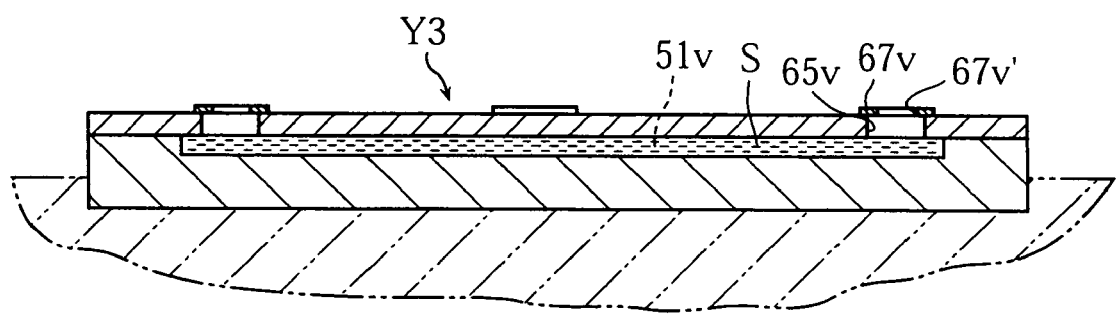
FIG. 38B and FIG. 38C are a sectional view and a plan view respectively for describing a sample introducing status.
Figure 38C:
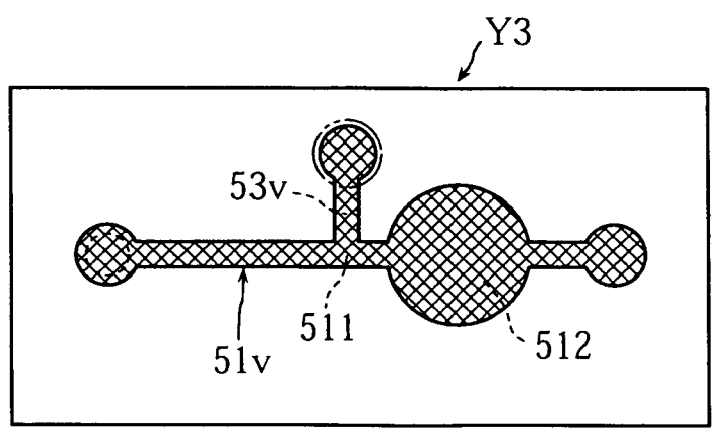

Next, as shown in FIG. 38A, the light source $2v$ is moved to above the sealing member $67v$ and the light is thrown to the sealing member $67v$ from the light source $2v$. As shown in FIG. 38B, an opening $67v'$ is formed in the sealing member $67v$ in this operation, which opens the gas releasing port $65v$. Once the gas releasing port $62v$ is open, capillarity occurs between the branching region 511 and in the gas releasing port $65v$, allowing the sample fluid S to move to the reactor 512 as shown in FIG. 38B and FIG. 38C. In the reactor 512, the sample fluid S reacts with the reagent in the reagent region 513, which leads to a specific colorization for example, in accordance with the amount of target component in the sample, or a specific amount of reactant is produced in accordance with the amount of target component in the sample. This gives the reactor 512 a specific light transparency (light absorbing characteristics) in accordance with the amount of target component in the sample.

In a predetermined time duration measured from the supply of the sample to the reactor 512, as shown in FIG. 39, the light source $2v$ is positioned above the reactor 512, and the light is thrown from the light source $2v$ to the reactor 512. The amount of light passing through the reactor 512 is measured by a light receiver 3. The analyzer X3 performs analysis, e.g. calculation of the concentration level of a target component based on the amount of light received by the light receiver 3.

According to the present mode of embodiment, only a simple arrangement is required in which the fluid entrance port $61v$ and the gas releasing ports $62v$, $65v$ are closed by the sealing members $66v$-$68v$ and throwing a light to the sealing members $66v$-$68v$, in order to control the closed/open status. Formation of the openings $66v'$-$68v'$ in the analyzing article Y3 does not very much complicate the construction of the analyzer X3, so it is possible to form the openings in the analyzing article Y3 without very much increasing the cost of manufacture. Further, the increase in cost and construction complexity in the analyzer X3 are reduced more reliably if the formation of the openings $66v'$-$68v'$ are made by using the light source which also throws light to the reactor 512 of the analyzing article Y3. Still further, use of a laser diode as the light source assures reliable formation of the openings $66v'$-$68v'$, which offers another advantage in terms of running cost.

Figure 40A:
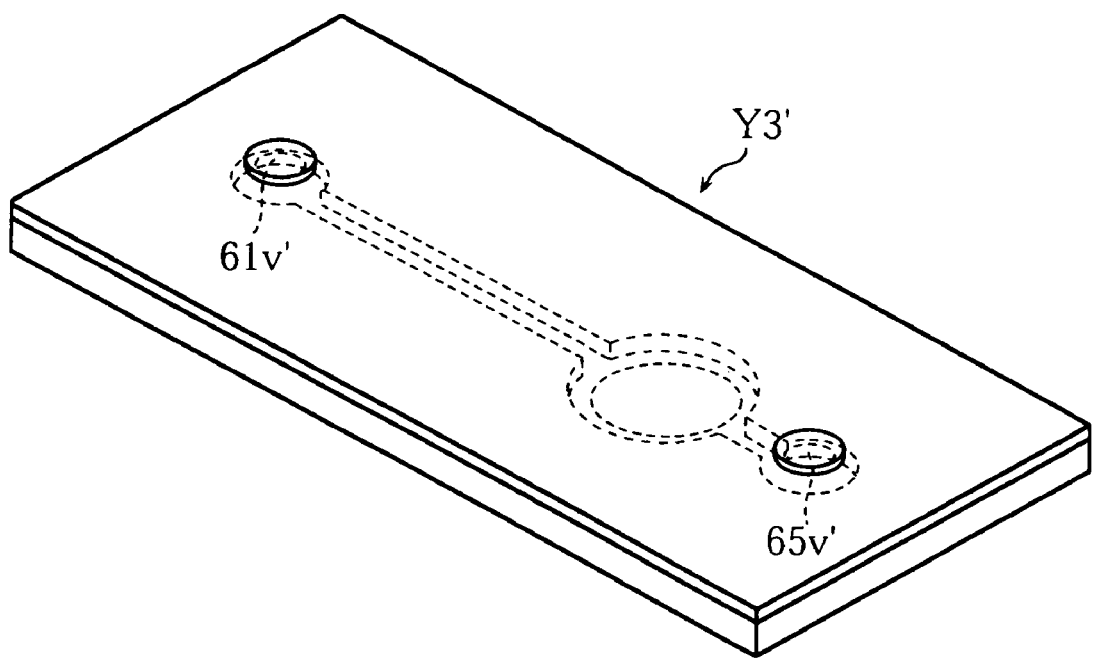
FIG. 40A and FIG. 40B are overall perspective views showing analyzing articles to which a method of forming an opening according to the present invention is applicable.
Figure 40B:
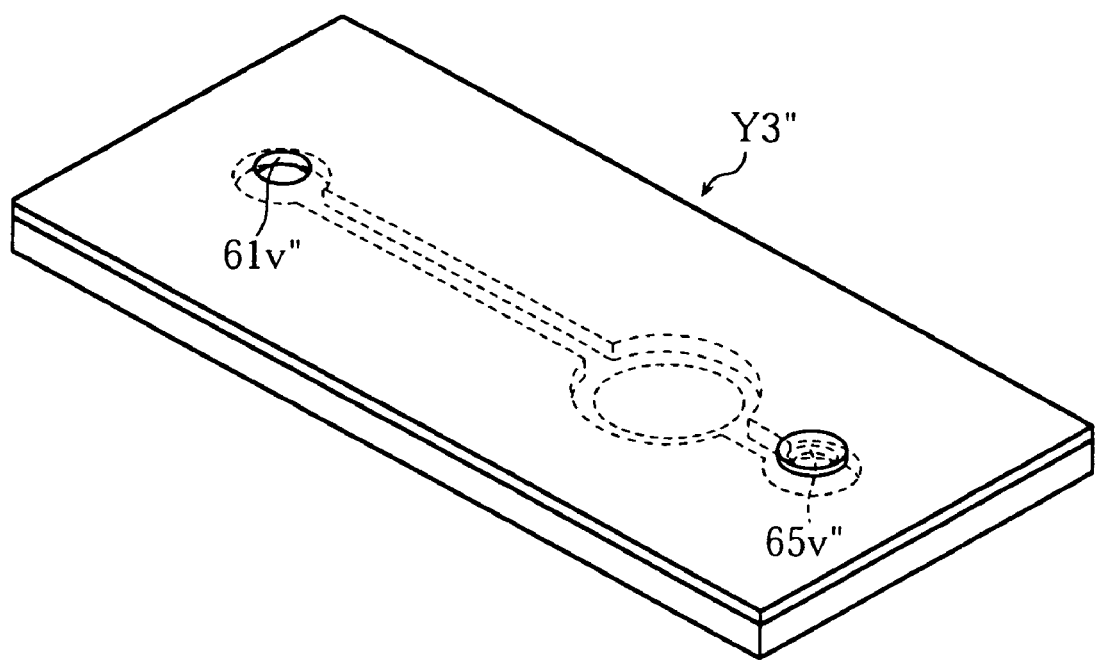

Obviously, the method of forming an opening according to the present invention is not limited to the modes of embodiment described above. For example, The present invention is applicable not only to the case where all of the fluid entrance port $61v$ and the gas releasing ports $62v$, $65v$ are covered by the sealing members $66v$-$68v$ but also to cases where at least one of the three openings $61v$, $62v$, $65v$ are sealed. Further, the present invention is applicable not only to the analyzing article Y3 which includes a branch passage $53v$ as shown in FIG. 32 but also to analyzing articles Y3', Y3" which do not include branch passages. Note that FIG. 40A shows an analyzing article Y3' which has both of its fluid entrance port $61v'$ and the gas releasing port $65v'$ closed, whereas FIG. 40B shows an analyzing article Y3" which has its gas releasing port $65v''$ closed.

In the first through the third modes of embodiment, description has been made using cases where the analysis is based on a light which has passed through the reactor. However, the present invention is also applicable to cases in which analysis is based on a reflected light from the reactor. Throwing of light to the reactors and measuring of the passing light may not necessarily be made individually for each reactor, but may be made all at once to a plurality of reactors.

The present invention is applicable to analysis made by using an analyzing article in which mobile components are transported by capillarity. Therefore, the present invention is applicable not only to those which use an optical method of analysis but also to those which use an electrochemical method of analysis. Further, application can be made also to methods in which a regent is transported instead of a sample, or in which a sample and a reagent are transported together with a carrier fluid. Obviously, the present invention is applicable not only to cases in which the analyzing article is a micro device but also to cases in which other types of analyzing articles are used.

EMBODIMENTS

Hereinafter, a discussion will be made whether or not a laser diode can make an opening in a sealing member.

Embodiment 1

Figure 41A:
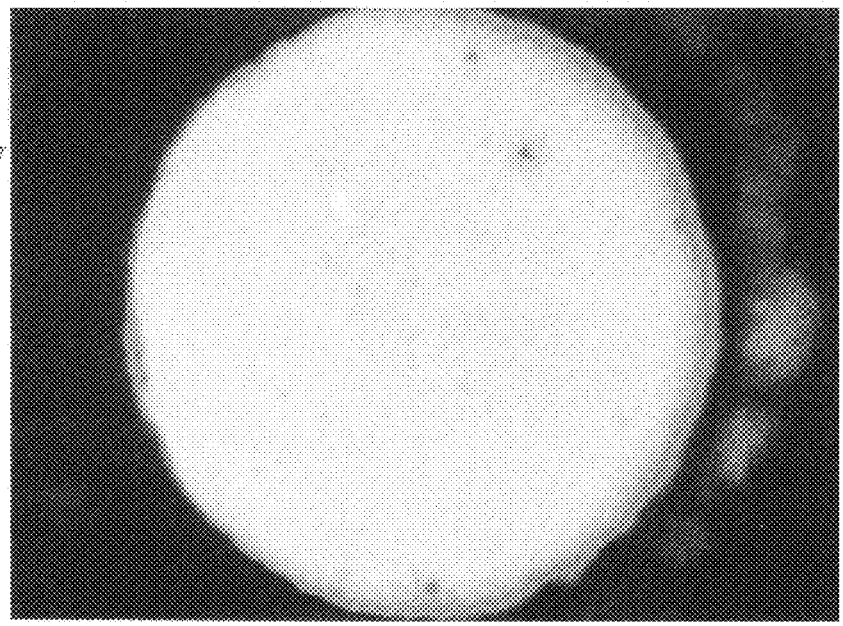
FIG. 41A and FIG. 41B are microscopic views of openings formed in a green resin sheet having a thickness of 10 μm.
Figure 41B:
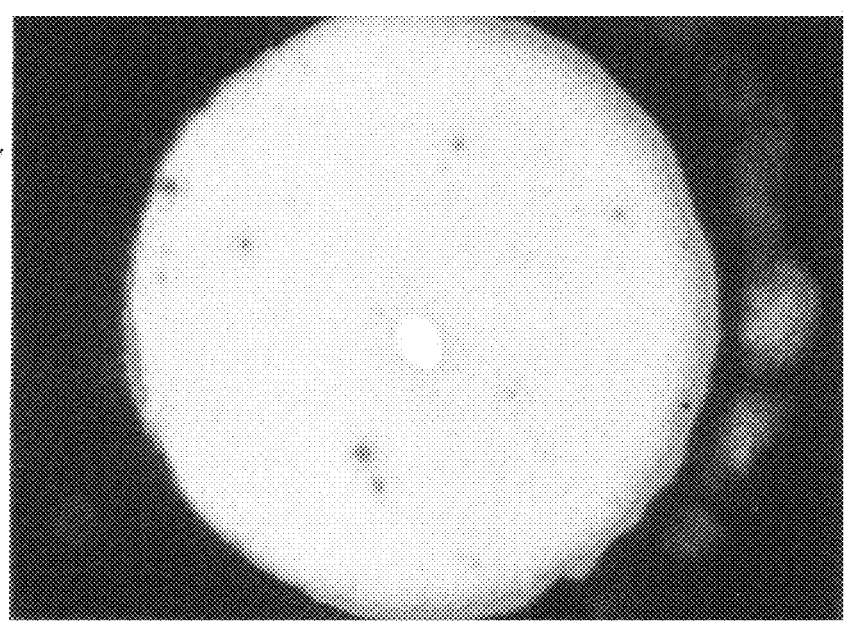

In the present embodiment, a laser diode unit manufactured by Sakai Glass Engineering Co., Ltd. was used to see if an opening can be formed in a green resin sheet. The laser diode unit incorporated, as the light source, a laser diode (HL6501MG; manufactured by Hitachi, Ltd.) which is capable of outputting a red light having a mean wavelength of 658 nm. The laser beam had a focal length of 3 mm, formed a spot of a 100 μm diameter at the focal point. The output of light from the laser diode was set to 27.5 mW, and the application time of the laser beam to the green sheet was varied as shown in Table 1. As for the green resin sheet, 100 weight parts of ethylene-vinyl acetate copolymer (EVA) (28% ethylene-vinyl acetate content, 58° C. melting point) hot melt sheet (manufactured by Nittoshinko Corporation) was mixed with a 2 weight parts of copper phthalocyanine serving as a green colorant, and the sheet thickness was controlled to be 10 μm. This green resin sheet absorbed a 658 nm wavelength light at a rate of 97%. Whether an opening was made or not was determined in a microscopic observation using a microscope (SZX9; manufactured by Olympus Optical Co., Ltd). Results are shown in Table 1, FIG. 41A and FIG. 41B. Each of FIG. 41A and FIG. 41B shows the green resin sheet magnified by 30 times after the laser beam was applied for 0.50 seconds and 0.60 seconds respectively.

TABLE 1

Green Resin Sheet (10 μm)

| Application Time (sec.) | Microscopic Observation |
|---|---|
| 0.40 | A small hole about to open. |
| 0.50 | A small hole formed (c. 0.1 mm) |
| 0.60 | A hole formed (c. 0.3 mm) |
| 0.70 | A hole formed (c. 0.3 mm) |
| 0.80 | A hole formed (c. 0.3 mm) |
| 0.90 | A hole formed (c. 0.3 mm) |
| 1.00 | A hole formed (c. 0.3 mm) |

Embodiment 2

Figure 42A:
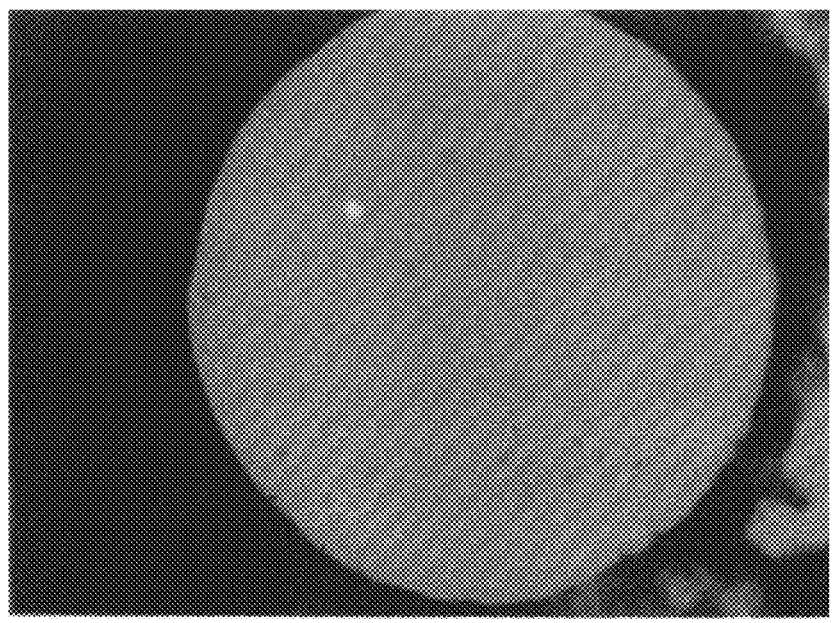
FIG. 42A and FIG. 42B are microscopic views of openings formed in a green resin sheet having a thickness of 50 μm.
Figure 42B:
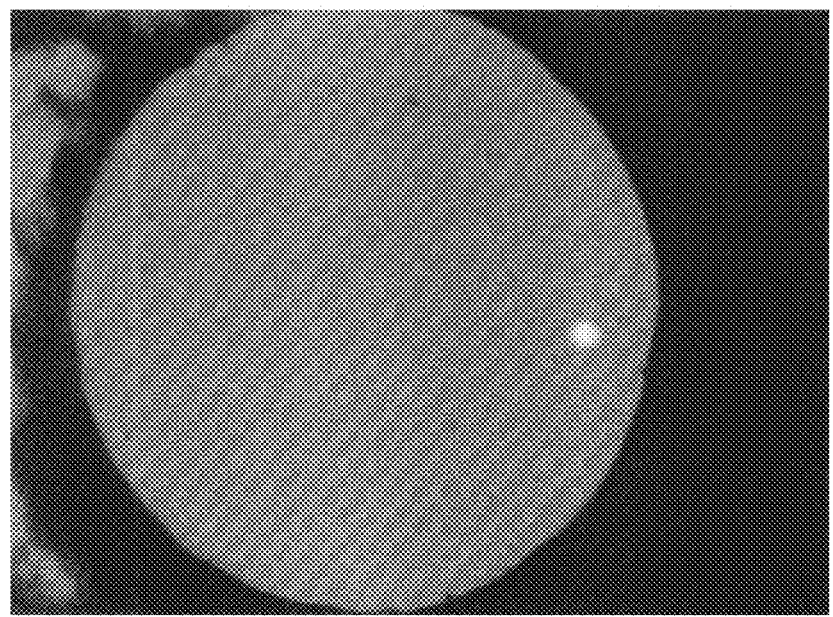
Figure 43A:
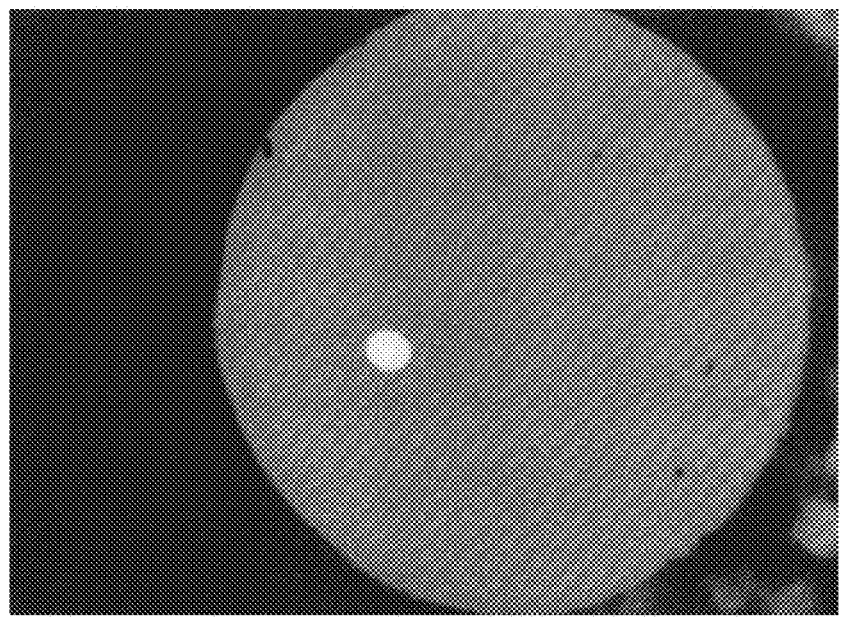
FIG. 43A and FIG. 43B are microscopic views of openings formed in a green resin sheet having a thickness of 50 μm.
Figure 43B:
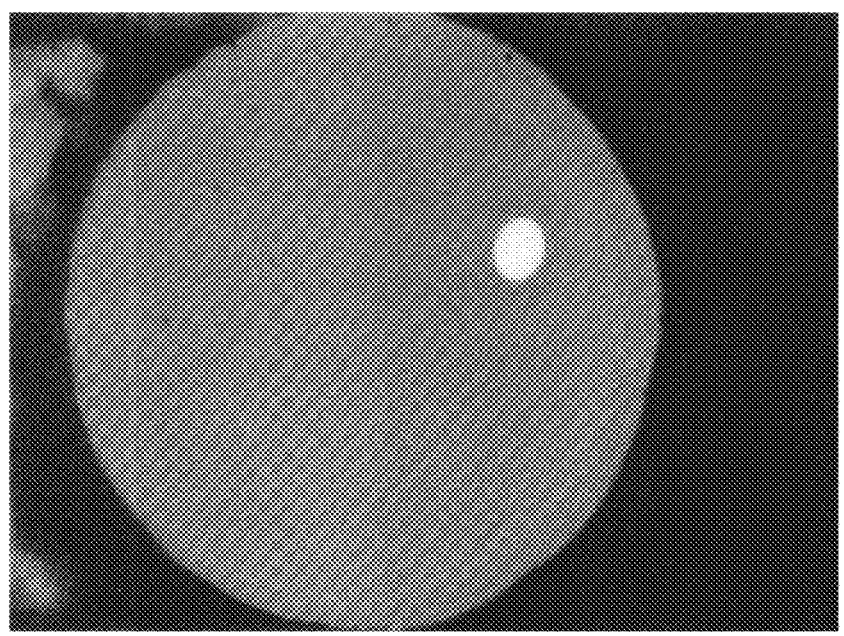

The present embodiment was identical with Embodiment 1, differing only in that the green resin sheet had a thickness of 50 μm (light absorption rate to the 658 nm wavelength light was about 100%), and that the laser application time was varied as shown in Table 2. Results are shown in Table 2, FIG. 42A, FIG. 42B, FIG. 43A and FIG. 43B. Each of FIG. 42A and FIG. 43B shows the green resin sheet magnified by 30 times after the laser beam was applied for 0.50 seconds, 0.80 seconds, 1.00 second and 2.00 seconds respectively.

TABLE 2

Green Resin Sheet (50 μm)

| Application Time (sec.) | Microscopic Observation |
|---|---|
| 0.50 | No holes. |
| 0.60 | No holes. |
| 0.70 | No holes. |
| 0.80 | No holes. |
| 0.90 | A hole formed (c. 0.1 mm) |
| 1.00 | A hole formed (c. 0.2 mm) |
| 1.10 | A hole formed (c. 0.2 mm) |
| 1.20 | A hole formed (c. 0.2 mm) |
| 2.00 | A hole formed (c. 0.4 mm) |

Embodiment 3

Figure 44A:
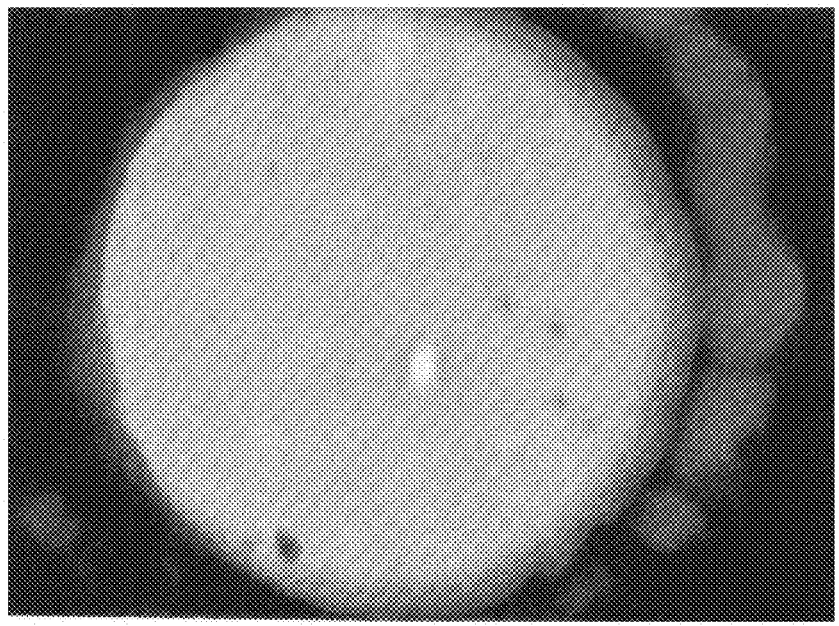
FIG. 44A and FIG. 44B are microscopic views of openings formed in a black resin sheet having a thickness of 10 μm.
Figure 44B:
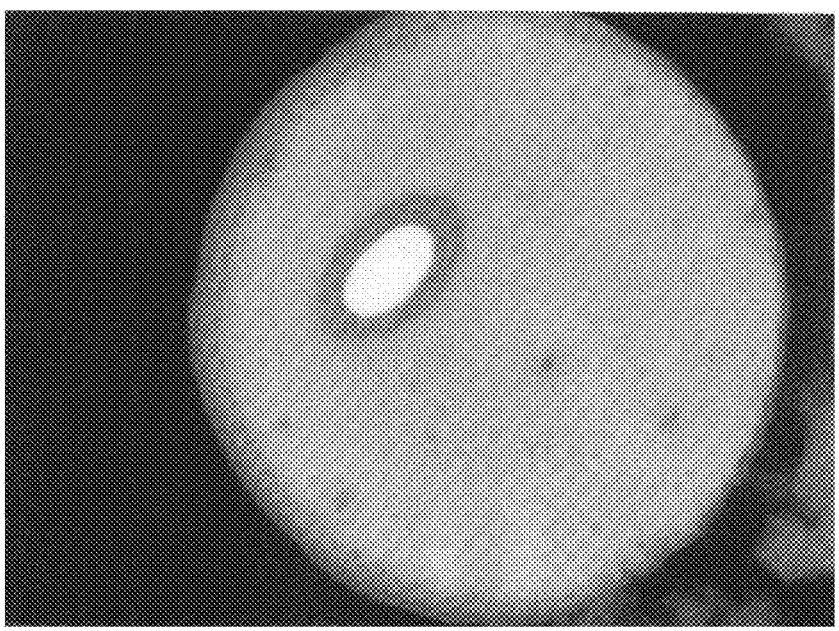
Figure 45:
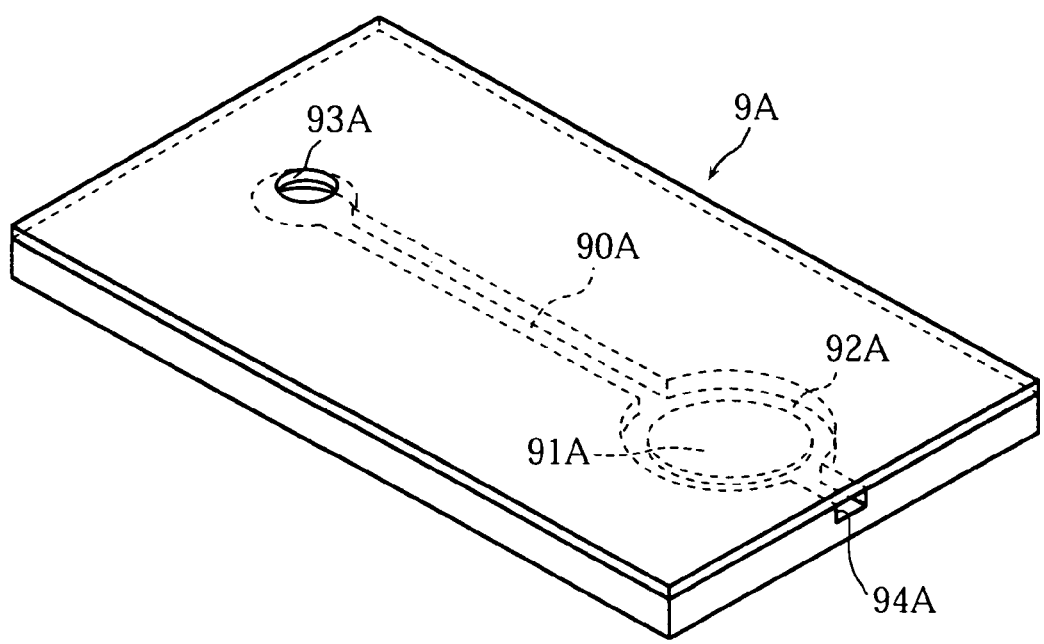
FIG. 45 is an overall perspective view for describing a conventional micro device.
Figure 46:
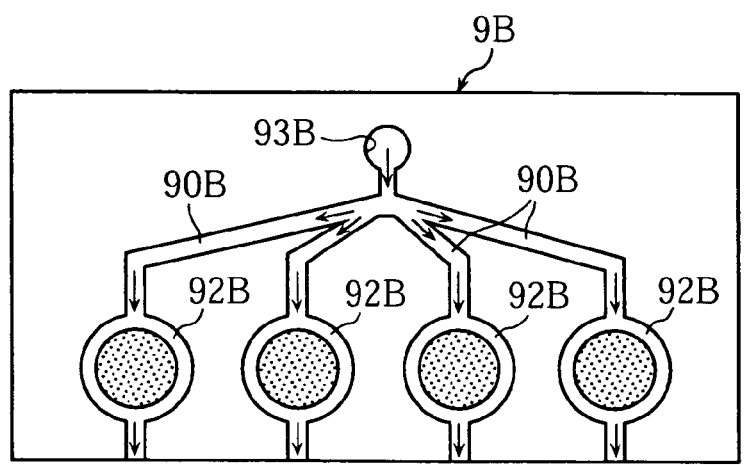
FIG. 46 is a see-through plan view for describing another conventional micro device.
Figure 47:
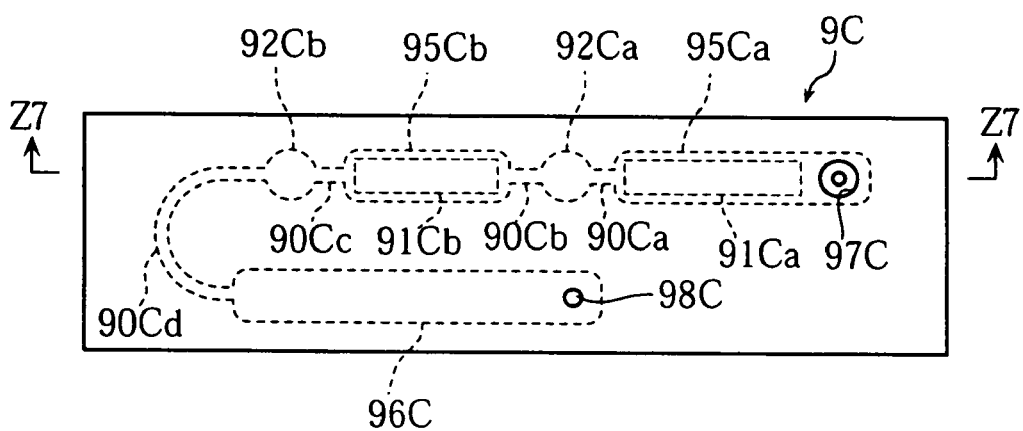
FIG. 47 is a plan view for describing a conventional micro device.
Figure 48:
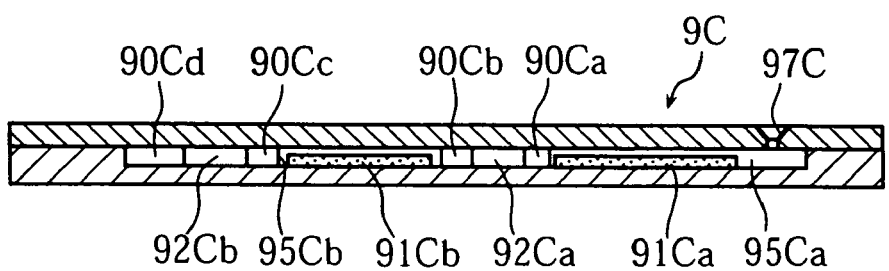
FIG. 48 is a sectional view taken in lines Z7-Z7 in FIG. 47.

In the present embodiment, observation was made to see if an opening can be formed in a black resin sheet by a laser beam. As for the black resin sheet, 100 weight parts of EVA were mixed with a 1.5 weight parts of carbon black serving as a black colorant, and the sheet thickness was controlled to be 10 μm. This black resin sheet absorbed a 658 nm wavelength light at a rate of about 99%. The laser beam was applied under the same conditions (except for the application time) as in Embodiment 1. Results are shown in Table 3. FIG. 44A and FIG. 44B each show the black resin sheet magnified by 30 times after the laser beam was applied for 1.0 second and 3.0 seconds respectively.

TABLE 3

Black Resin Sheet (10 μm)

| Application Time (sec.) | Microscopic Observation |
|---|---|
| 1.00 | A small hole formed (>0.1 mm) |
| 2.00 | A small hole formed (>0.1 mm) |
| 3.00 | A small hole formed (>0.1 mm) |
| 3.50 | A hole formed (c. 0.4 mm) |
| 4.00 | A hole formed (c. 0.8 mm) |

[Discussion on the Results]

In Embodiment 1, in which the laser diode output was 27.5 mW and the beam was applied to a green resin sheet (sheet thickness 10 μm, light absorption rate about 97%), as understood from Table 1, FIG. 41A and FIG. 41B, it was learned that an opening is formed when the laser application time was not shorter than 0.5 seconds. In Embodiment 2, in which the beam was applied to a green resin sheet (sheet thickness 50 μm, light absorption rate about 100%), as understood from Table 2, FIG. 42A, FIG. 42B, FIG. 44A and FIG. 43B, it was learned that an opening is formed when the laser application time was not shorter than 0.9 seconds. Thus, as long as the resin sheet has a near 100% light absorption rate and a thickness between the recess 10-50 μm range, it is possible to make a sufficient opening with a relatively small output of 27.5 mW and in a short time of about 1.0 second.

In Embodiment 3, in which the beam was applied to a black resin sheet (sheet thickness 10 μm, light absorption rate about 99%), as understood from Table 3, FIG. 44A and FIG. 44B, it was learned that a sufficient opening is formed by laser application for a few seconds if the application is made under the same conditions (except for the application time) as in Embodiment 1 and Embodiment 2.

As described, a laser beam applied for a relatively short time can form an opening in a resin sheet, if the resin sheet is a thermoplastic resin having a low melting point and an increased light absorption rate by an addition of colorant.

The invention claimed is:

1. An analyzer for analysis of a sample comprising:
an analyzing article including a plurality of individual passages each for moving a mobile component from a fluid reservoir via a first goal to a second goal, a common passage extending from each individual passage to another for connecting the plurality of individual passages downstream from the second goal of each individual passage in a flow direction of the mobile component, and an analyzer unit for analyzing the mobile component of the sample,
the analyzing article preventing the mobile component from moving beyond the first goal in the passage while allowing the mobile component to move beyond the first goal to the second goal in each individual passage by opening a common gas release port communicating with the common passage, the common gas releasing port being closed by a common closer, wherein the analyzer further comprises an common opener for opening the common gas release port at the downstream location, wherein each individual passage extends horizontally throughout an entire path from the fluid reservoir to the common passage, and wherein the analyzing article comprises a substrate formed with the plurality of individual passages, and a cover attached to the substrate for covering the plurality of individual passages, the common passage being formed in the cover above the plurality of individual passages and configured to prevent the mobile component of the sample from flowing into the common passage.

2. The analyzer according to claim 1, wherein the analyzing article allows communication between inside of each individual passage and outside,
the common opener opening the common gas releasing port by forming an opening in the common closer.

3. The analyzer according to claim 2, wherein the common closer is provided by a sheet member,
the common opener including a cutter for cutting the sheet member.

4. The analyzer according to claim 2, wherein the common closer is provided by a plug member inserted into the common gas releasing port,
the common opener including a puller for pulling out the plug member.

5. The analyzer according to claim 1, wherein the common opener applies energy to the analyzing article without contacting the analyzing article for melting or deforming at least part of the analyzing article.

6. The analyzer according to claim 1,
wherein the analyzing article further includes a branch passage branched from a branching region in each individual passage to provide the first goal, the branch passage communicating with outside for preventing the mobile component from moving in each individual passage beyond the branching region.

7. The analyzer according to claim 6, wherein the common closer includes a movable closing element for removable insertion into the common gas release port.

* * * * *